United States Patent
Gerloni

(12) 
(10) Patent No.: US 10,993,949 B2
(45) Date of Patent: May 4, 2021

(54) 17α-MONOESTERS AND 17α,21-DIESTERS OF CORTEXOLONE FOR USE IN THE TREATMENT OF TUMORS

(71) Applicant: COSMO TECHNOLOGIES LTD., Dublin (IE)

(72) Inventor: Mara Gerloni, San Diego, CA (US)

(73) Assignee: COSMO TECHNOLOGIES LIMITED, Dublin (IE)

(*) Notice: Subject to any disclaimer, the term of this patent is extended or adjusted under 35 U.S.C. 154(b) by 0 days.

(21) Appl. No.: 16/820,407

(22) Filed: Mar. 16, 2020

(65) Prior Publication Data
US 2020/0215080 A1 Jul. 9, 2020

Related U.S. Application Data

(60) Continuation of application No. 16/199,015, filed on Nov. 23, 2018, now Pat. No. 10,646,497, which is a division of application No. 15/517,653, filed as application No. PCT/EP2015/073172 on Oct. 7, 2015, now Pat. No. 10,183,030.

(30) Foreign Application Priority Data

Oct. 8, 2014 (EP) .................................. 14188063.3

(51) Int. Cl.
| | | |
|---|---|---|
| A61K 31/573 | (2006.01) | |
| C07J 5/00 | (2006.01) | |
| A61K 9/00 | (2006.01) | |
| A61K 45/06 | (2006.01) | |

(52) U.S. Cl.
CPC .......... *A61K 31/573* (2013.01); *A61K 9/0019* (2013.01); *A61K 9/0053* (2013.01); *A61K 45/06* (2013.01); *C07J 5/0053* (2013.01)

(58) Field of Classification Search
CPC ... A61K 31/573; A61K 9/0019; A61K 9/0053
See application file for complete search history.

(56) References Cited

U.S. PATENT DOCUMENTS

| | | | |
|---|---|---|---|
| 3,152,154 A | 10/1964 | Ercoli et al. | |
| 3,530,038 A | 9/1970 | De Flines et al. | |
| 4,260,464 A | 4/1981 | Kerb et al. | |
| 4,472,393 A | 9/1984 | Shapiro | |
| 5,990,099 A | 11/1999 | Clark | |
| 6,172,054 B1 | 1/2001 | Clark | |
| 7,186,753 B1 | 3/2007 | Del Soldato | |
| 7,687,484 B2 | 3/2010 | Bodor | |
| 8,143,240 B2 | 3/2012 | Ajani et al. | |
| 8,785,427 B2 * | 7/2014 | Mauro .................... | A61P 25/00 514/181 |
| 2009/0240049 A1 | 9/2009 | Villa et al. | |
| 2014/0199236 A1 | 7/2014 | Chen et al. | |

FOREIGN PATENT DOCUMENTS

| | | |
|---|---|---|
| BE | 619180 A | 12/1962 |
| BE | 619180 A1 | 12/1962 |
| CN | 101397317 A | 4/2009 |
| DE | 4121484 A1 | 1/1993 |
| DE | 1020060590063 A1 | 6/2007 |
| JP | 5470253 A | 6/1979 |
| JP | 2005504762 A | 2/2005 |
| RU | 2482190 C2 | 5/2013 |
| RU | 2506974 C1 | 2/2014 |
| WO | 8809337 A1 | 12/1988 |
| WO | 9009394 A2 | 8/1990 |
| WO | 0049993 A2 | 8/2000 |
| WO | 0240030 A1 | 5/2002 |

(Continued)

OTHER PUBLICATIONS

Japanese Office Action with English Translation, issued in corresponding Japanese Application No. 2019-006199, dated Mar. 3, 2020, 11 pages.
Celasco et al., "Pharamacoligical profile of a 9,11-Dehydrocortexolone 17α-Butyrate (CB-03-04), a New Androgen Antagonist with Antigonadotropic Activity" Arzneim.-Forshe/Drug Res., vol. 55, No. 10, 2005, 7 pages.
Search Report and Written Opinion dated Dec. 8, 2018 in PCT/EP2015/073172 (16 pages).
Search Report dated Mar. 27, 2015 issued in counterpart European Patent Application No. 14188063.3 (11 pages).
G.Celascoa et al. "Pharmacological Profile of 9,11-Dehydrocortexolone 17[alpha]-Butyrate (CB-03-04), a New Androgen Antagonist with Antigonadotropic Activity", Drug Research, Jan. 2005, pp. 581-587, vol. 55, No. 10.

(Continued)

*Primary Examiner* — Pancham Bakshi
(74) *Attorney, Agent, or Firm* — Rothwell, Figg, Ernst & Manbeck, P.C.

(57) ABSTRACT

The present invention relates to certain cortexolone derivatives of formula (I)

and the use of the same as antitumor active ingredients for the curative or adjuvant, or neoadjuvant or palliative treatment of precancerous lesions, dysplasias, metaplasias and tumor diseases, including malignant neoplasias and metastasis. The present invention also relates to pharmaceutical compositions comprising cortexolone derivatives of formula (I) as active ingredients and at least one physiologically acceptable excipient, and to the use of the pharmaceutical compositions as antitumor medicinal products.

2 Claims, 20 Drawing Sheets

(56) References Cited

FOREIGN PATENT DOCUMENTS

| WO | 03014141 A1 | 2/2003 |
|---|---|---|
| WO | 2007031349 A1 | 3/2007 |
| WO | 2007142842 A2 | 12/2007 |
| WO | 2009019138 A2 | 2/2009 |
| WO | 2009076170 A2 | 6/2009 |
| WO | 2011151252 A2 | 12/2011 |
| WO | 20120129305 A1 | 9/2012 |
| WO | 2016055537 A1 | 4/2016 |

OTHER PUBLICATIONS

P. Ferraboschi et al. "Lipase-catalyzed preparation of corticosteroid 17alpha-esters endowed with antiandrogenic activity", Tetrahedron Letters, Jul. 2008, pp. 4610-4612, vol. 49, No. 31.

T. Corbishley et al. "Androgen receptor in human normal and malignant pancreatic tissue and cell lines", Cancer, May 1986, pp. 1992-1995, vol. 57, No. 10.

Peterson, R. E.: "Billary excretion of neutral steroids in man" Biliary System, Symp. Nato Advan. Study Inst., Newcastle-Upon-Tyne, England, 1963, 385, published in 1965, abstract only, retrieved from Accession No. 1966:87023, (2 pages).

J.J. Keating et al. "A prospective randomised controlled trial of tamoxifen and cyproterone acetate in pancreatic carcinoma", British Journal of Cancer, Nov. 1989, pp. 789-792, vol. 60, No. 5.

P. Ferraboschi et al."A full conformational characterization of antiandrogen cortexolone-17[alpha]-proplonate and related compounds through theoretical calculations and nuclear magnetic resonance spectroscopy", Medchemcomm, Apr. 2014, pp. 904-914, vol. 5, No. 7.

Cutler, Gordon B., Jr. et al: "11-Deoxycortisol: a glucocorticoid antagonist in vivo", Endocrinology, 104:1839, abstract only, retrieved from STN Database Accession No. 1979:469056, (2 pages).

S. Inagaki "17 alpha Hydroxy Progesterone Caproate", J. Wakayam Med. Assoc., vol. 22,No. 3, May 1972, pp. 181-205.

R.M. Kelley et al. "The Role of Progesterone in Human Endometrial Cancer". Cancer Research, vol. 25, 1965, pp. 1190-1192.

A. Varga et al. "Effect of 17-alpha hydroxyprogesterone 17-n-caproate on Various Pelvic Malignanci", Obstetrics and Gynecology, vol. 23, No. 1, Jan. 1964, pp. 51-62.

S. Patel et al. "Effect of 17-alpha hydroxyprogesterone caproate on the production of tumor necrosis factor-alpha and the expression of cyclooxygenase-2 in lipopolysaccharide-treated gravid human myometrial explants", Journal of Perinatalogy, 2010, vol. 30, pp. 584-589.

G.Celasco et al. "Biological Profile of Cortexolone 17-alpha Propionate (CB-03-01), a New Topical and Peripherally Selective Androgen Antagonist", Arzneim-Forsch/Drug Research, vol. 54, No. 12, 2004, pp. 881-886.

The extended European Search Report issued in Application No. 18198653.0 dated Feb. 18, 2019, 11 pages.

Ekins, S. et al., "Challenges Predicting Ligand-Receptor Interactions of Promiscous Proteins: The Nuclear Receptor PXR", PLOS Computational Biology, vol. 5, No. 12, Dec. 11, 2009, pp. e1000594-1, XP05554963, KP055549646, XP055549647, 23 pages.

Bonsman, U. et al., "Metabolisation and receptor affinity of topically applied esters of glucocorticoids", Database Embase [Online], Elsevier Science Publishers, Amsterdam, NL, 1998, XP002788474, 3 pages.

Russian Office Action with Search Report issued in Application No. 2017115773/04 dated Mar. 15, 2019, 8 pages.

Vitali, R et al., "Esteri del 17alpha-ossiprogesterone e derivati di sostituzione, Nuova via d"accesso e nuovi derivati", Gazzette Chimica Italiana, vol. 96, 1966, 1115-1120. (English Abstract).

Greenway, B. A., "Effect of flutamide on survival in patients with pancreatic cancer: results of a prospective andomised, double blind, placebo controlled trial", BMJ, 1998, vol. 316, pp. 1935-1938.

Lehmann, B. D. et al., "Identification of human triple-negative breast cancer subtypes and preclinical models for , election of targeted therapies", The Journal of Clinical Investigation, 2011, vol. 121, pp. 2750-2767.

Gucalp, A. et al., "Phase II trial of bicalutamide in patients with androgen receptor-positive, estrogen receptor-negative metastatic breast cancer", Clinical Cancer Research, 2013, vol. 19, pp. 5505-5512.

Hoffmann, J. et al., "Steriodhormone receptors as targets for the therapy of breast and prostate cancer-recent 1: advances, mechanisms of resistance, and new approaches", Journal of Steroid Biochemistry & Molecular Biology, ?005, vol. 93, pp. 191-200.

Japanese Office Action issued in Application No. 2017-518978 dated May 28, 2019, with translation, 10 pages.

Wikipedia "Adenocarcinoma" printed Dec. 30, 2019, 6 pages, http://en.wikipedia.org/wiki/adenocarcinoma.

Horoszewicz, Julius S. et al., "LNCaP Model of Human Prostatic Carcinoma", Cancer Research 43, Apr. 1963, pp. 1809-1818.

Gray, Michael J., et al., "Neuropilin-1 Suppresses Tumorigenic Properties in a Human Pancreatic Adenocarcinoma Cell Line Lacking Neuropilin-1 Coreceptors", Cancer Research 65: (9), May 1, 2005 , pp. 3664-3671.

Hierowski, Marion T., "Stimulation by somatostatin of dephosphorylation of membrane proteins in pancreatic cancer MIA PaCa-2 cell", FEBS 2129, vol. 179, No. 2, Jan. 1985, pp. 252-256.

Deer, Emily L. MD, et al., "Phenotype and Genotype of Pancreatic Cancer Cell Lines", NIH Public Access, Pancreas: 39 (4): May 2010, pp. 425-435.

Shoyab Mohammed, et al., "Amphiregulin: A bifunctional growth-modulating glycoprotein produced by the phorbol 12-myristate 13-acetate-treated human breast adenocarcinoma cell line MCF-7", Proc. Natl. Acad. Sci., USA, vol. 85, Sep. 1968, pp. 6528-6532.

HMS LINCS Database "HMS LINCS Project", https://lincs.hms.harvard.edu/db/cells/50058/, accessed Dec. 30, 2019 6 pages.

Zhang Huanle, et al., "MicroRNA expression profile of colon cancer stem-like cells in HT29 adenocarcinoma cell line", Biochemical and Biophysical Research Communication, 404 (2011) pp. 273-278.

\* cited by examiner (a) PC-3 Prostate (b) LNCaP Prostate (c) MiaPaca-2 Pancreatic (d) Panc-1 Pancreatic

| Cancer cell line | Relative AR Expression |
|---|---|
| PC-3 | 1 |
| MiaPaca-2 | 1 |
| Panc-1 | 2 |
| LNCaP | 5 |

17α-MONOESTERS AND 17α,21-DIESTERS OF CORTEXOLONE FOR USE IN THE TREATMENT OF TUMORS

CROSS REFERENCE TO RELATED APPLICATIONS

The instant application is continuation of U.S. patent application Ser. No. 16/199,015, filed on 23 Nov. 2018, which in turn is a division of U.S. patent application Ser. No. 15/517,653, filed on 7 Apr. 2017, now U.S. Pat. No. 10,183,030, which in turn is a national stage filing under 35 U.S.C. § 371 of PCT/EP2015/073172, filed on 7 Oct. 2015, and claims the benefit of priority to European Patent Application No. 14188063.3, filed 8 Oct. 2014. Each application is incorporated herein by reference in its entirety.

SUMMARY OF THE INVENTION

The present invention provides certain cortexolone derivatives of formula (I):

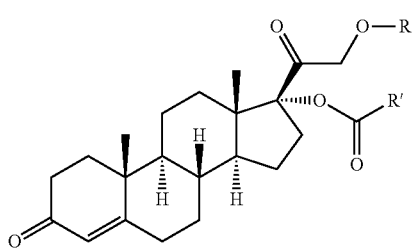

and the same for use as antitumor active ingredients for the curative or adjuvant, or neoadjuvant or palliative treatment of precancerous lesions, dysplasias, metaplasias and tumor diseases, including malignant neoplasias and metastasis.

Another aspect of the invention relates to pharmaceutical compositions comprising at least one cortexolone derivative of formula (I) as active ingredient with at least one physiologically acceptable excipient, and to the same pharmaceutical compositions for use as antitumor medicinal products for the curative or adjuvant, or neoadjuvant or palliative treatment of precancerous lesions, dysplasias, metaplasias and tumor diseases, including malignant neoplasias and metastasis.

BACKGROUND OF THE INVENTION

Tumor, or neoplasm, is defined as a mass of new tissue which persists and grows independently of its surrounding structures, and which has no physiological use (Doreland's Medical Dictionary, 23 ED. 1960).

Several classifications are available for tumors: for the exploitation of this patent application, the most important are the epithelial tumors.

The epithelial tumors are neoplasms derived from epithelial cells, the type of cell which lines hollow internal organs and body surfaces; this group includes many of the most common cancers, and includes most of those developing in the breast, prostate, lung, pancreas, and gastrointestinal tract.

In some cases, the epithelial tumors can also be characterized by the presence of specific hormone-receptors in the tumor cells which gives to the tumor a hormone-sensitivity.

Carcinomas, that are malignant tumors derived from epithelial cells, make up about 85 out of every 100 cancers (85%).

One example of epithelial carcinoma is the pancreatic carcinoma (also referred to as pancreatic cancer).

Pancreatic cancer is one of the most deadly forms of carcinomas. The exocrine and endocrine cells of the pancreas form completely different types of tumors. Exocrine pancreatic tumors constitute the most common type of pancreatic cancer (more than 95%). Although benign (non-cancerous) cysts and benign tumors (adenomas) may develop in the pancreas, most of the exocrine pancreatic tumors are malignant.

The carcinoma of pancreas, particularly exocrine pancreas carcinoma and much more particularly the most frequent one, that is ductal adenocarcinoma, falls into the five most frequent causes of death in males, and is the fourth cause of death in females. It is one of the tumors with the highest unfavorable prognosis, with a survival of only 5% in males and 6% in the females at 5 years after diagnosis. The highest incidence occurs between 60-70 years of age (AIOM. Linea Guida Carcinoma del Pancreas Esocrino, ed. 2013).

The etiology of the exocrine pancreas carcinoma is unknown. There is a recognized genetic predisposition (familiarity) and some risk factors such as smoke, fatty diet, diabetes mellitus type 2, chronic pancreatitis, environmental factors such as solvents or pesticides.

The carcinoma of the exocrine pancreas is, in its early stage, asymptomatic, and this explains the delay in the diagnosis, which is usually performed when the disease is at an advanced stage, with exception for accidental detection during diagnostic procedures for other abdominal diseases.

Patients diagnosed with pancreatic cancer typically have a poor prognosis: considering the above described delay in the diagnosis, only about 15% of cases show the tumor limited to the pancreas, whereas in the remaining cases, the diffusion to the loco-regional lymphnodes is detected in about 25% of the patients, and the presence of metastases is detected in 60% of the cases.

Median survival from diagnosis of the cancer is approximately three to six months, while a five-year survival is significantly less than 5%.

The therapy of carcinoma of the pancreas is surgery, when possible, also with palliative purposes.

Radical pancreaticoduodenectomy is currently the only chance of cure, especially for minimal disease.

The medical therapy, also associated to radiotherapy, is limited to the unresectable cases, or when metastases are present, or as adjuvant treatment after surgery. Although there are occasional reports of individual patients who respond to gemcitabine or fluorouracil, or combination regimens with doxorubicin, methotrexate, cisplatin, oxaliplatin, irinotecan, erlotinib and so on, the results of chemotherapy are generally unsatisfactory and often no better than no treatment at all (Martindale, 31 ed., page 530).

Theve et al, in 1983 reviewed possible effects of sex hormones on the pancreas, based on reports on steroid receptor proteins in pancreatic tissue, the high capacity of estrogen binding protein in the human pancreas and capacity of human pancreatic tissue to convert the main peripheral estrogen, estrone sulphate, into the terminal biologically active estradiol-17 beta.

With this background, they tried tamoxifen (an antagonist of the estrogen receptor) in patients with unresectable adenocarcinoma of the pancreas with some preliminary results similar to those by Wong et al., in 1993.

The clinical practice in the subsequent years did not give the expected results, but the conclusion was that even if anti-estrogens did not constitute the optimal form of therapy, other sorts of hormonal manipulation ought to be tried in pancreatic cancer.

In view of the above, there is a strong need for new approaches of tumor treatment and, in particular, for the treatment of carcinomas, and still more especially for the treatment of epithelial tumors, especially prostatic carcinoma or pancreas carcinoma (preferably exocrine pancreas carcinoma).

A number of compounds referred to as 17α-monoesters, 21-monoesters and 17α,21-diesters of cortexolone and processes for their manufacturing are known in the art.

WO03/014141 describes compounds belonging to the family of steroids structurally related to cortexolone (also known as 11-deoxycortisone) as having mainly antiandrogenic activity. These compounds, such as cortexolone 17α-propionate, act by interfering with the direct action of the androgenic hormones on the Androgen Receptor (AR) in the tissues.

WO2007/031349 discloses $C_3$-$C_{10}$ 17α-esters of 9,11-dehydrocortexolone, a derivative structurally related to cortexolone, as antigonadotrophic agent, which may be useful for the treatment disorders closely related to excess of gonadotrophin production.

WO2009/019138 discloses an enzymatic process for the obtainment of 17α-monoesters of cortexolone and of 9,11-dehydrocortexolone; furthermore, it also discloses the existence of several crystalline forms of cortexolone 17α-propionate, namely crystalline form I, form II, form III and hydrate form IV, and certain processes to obtain them.

Cyproterone acetate (abbreviated as CPA), is a synthetic steroid, which was considered as the standard therapy for the treatment of androgen-sensitive tumors, especially prostate cancer. The standard therapy with Cyproterone Acetate resulted quite ineffective in the tumors with reduced, or absent, expression of Androgen Receptor (Br. J. Cancer (1989), 60, 789-792).

It is known in the art that the presence of 17α-esterification confers to cortexolone 17α-esters different antiandrogenic activities, demonstrated in animals (Celasco et al., Arzneim-Forsch 2005; 5: 581-7).

It has now been surprisingly found that cortexolone 17α(alpha)-monoesters, 21-monoesters and 17α(alpha),21-diesters have unexpected antitumor effects, both in isolated cancer cell lines in vitro and in xenograft prostate and pancreatic cancer model in vivo into the animals.

The antitumor effect of the invention was evident both in carcinoma cells harboring Androgen Receptor (AR+), such as in the case of prostate cancer cells LNCaP or pancreatic cancer cells Panc1, and, very surprisingly, also in cells with absent, or reduced, expression of the Androgen Receptor (AR−), as prostate cancer cells PC3, or pancreatic cancer cells MiaPaca. The antitumor effect of the invention was also evident in mammary carcinomas (AR−), and gastrointestinal tract carcinomas (AR−).

BRIEF DESCRIPTION OF THE FIGURES

The invention will now be described by the following non-limiting figures and examples.

DEFINITIONS

Figure 1:
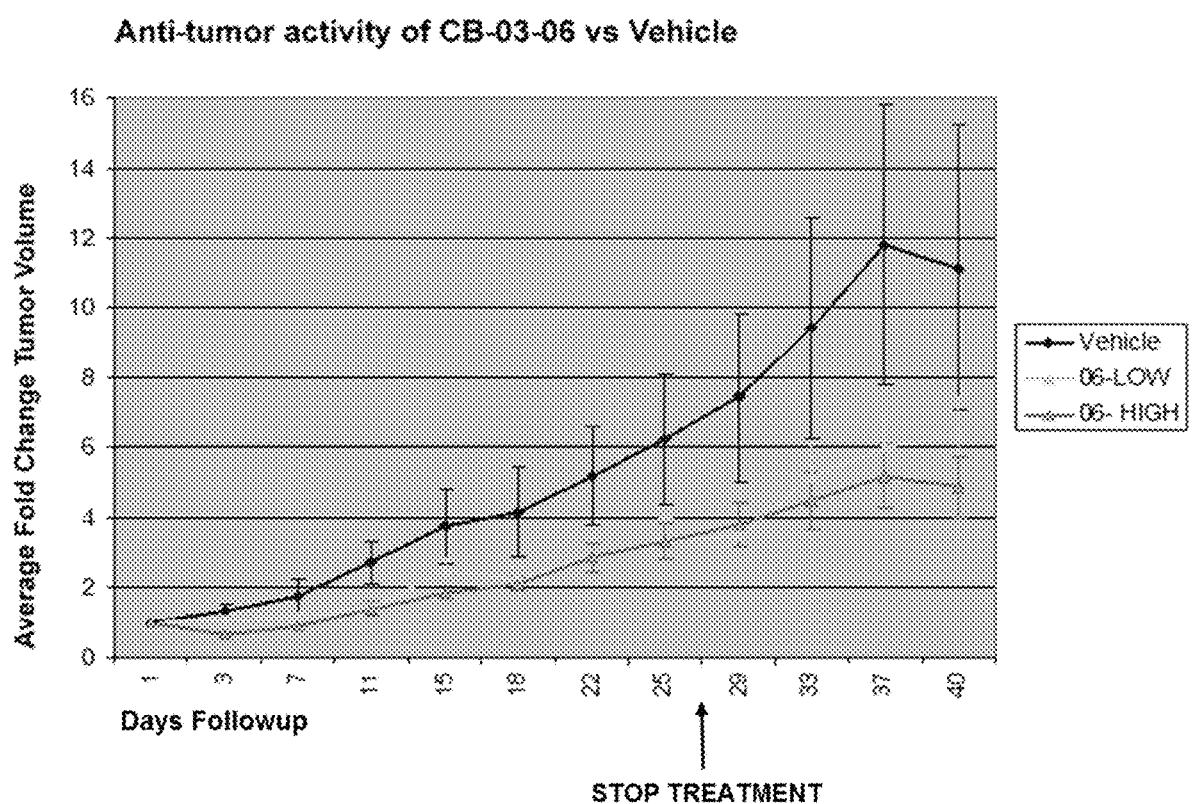
FIG. 1: Average fold change in pancreatic tumor volume, measured relative to the start of subcutaneous (SC) treatment, in the xenograft animal model of nude mice (MiaPaca pancreatic cell line) with cortexolone 17α-benzoate (in the figure referred to as "06" and as "CB-03-06") at low dose (230 μM) and at high dose (1150 μM). Reference to "Vehicle" is a control treated group with 0.4% (v/v) tween 80 and 0.5% (w/v) carboxymethylcellulose in normal saline. Mice were treated with the compound and vehicle SC daily for 28 consecutive days. The stop treatment arrow refers to the day when the treatment was ended.

Unless otherwise defined, all terms of art, notations and other scientific terminology used herein are intended to have the meanings commonly understood by those skilled in the art to which this disclosure pertains. In some cases, terms with commonly understood meanings are defined herein for clarity and/or for ready reference; thus, the inclusion of such definitions herein should not be construed to represent a substantial difference over what is generally understood in the art.

In particular, the terms "physiologically acceptable excipient" or "pharmaceutically acceptable excipient" herein refer to a substance devoid of any pharmacological effect of its own and which does not produce adverse reactions when administered to a mammal, preferably a human. Physiologically acceptable excipients are well known in the art and are disclosed, for instance in the Handbook of Pharmaceutical Excipients, sixth edition (2009), herein incorporated by reference.

The term "alkyl" as used herein means a saturated straight or branched chain hydrocarbon.

The term "aryl" herein refers to aromatic mono- and poly-carbocyclic ring systems, wherein the individual carbocyclic rings in the poly-carbocyclic ring systems may be fused or attached to each other via a single bond. Suitable "aryl" groups comprise, but are not limited to, phenyl, naphthyl, biphenyl, and the like.

The term "heteroaryl" herein refers to an aromatic mono- and poly-carbocyclic ring system comprising at least a heteroatom in the ring system, wherein said heteroatom is selected in the group comprising, but not limited to, nitrogen, sulphur, oxygen and the like, and wherein the individual cyclic rings in the poly-carbocyclic ring systems may be fused or attached to each other via a single bond. Suitable "heteroaryl" groups comprise, but are not limited to, pyridyl, imidazolyl, pyrrolyl, furyl, benzimidazolyl, thiofuranyl and the like.

Aryl groups may be optionally substituted in at least one of the carbon atoms of the ring with a group selected from lower alkyl, lower alkenyl, lower haloalkyl, lower haloalkenyl, lower alkoxy, lower halcalkenyl, lower alkenyloxy, halogen, nitro, cyano, lower alkylthio, and the like.

Heteroaryl groups may be optionally substituted in at least one of the carbon atoms or in at least one of the heteroatoms of the ring with a group selected from lower alkyl, lower haloalkyl, lower alkoxy, lower alkenyl, lower halcalkenyl, lower alkenyloxy, halogen, nitro, cyano, lower alkylthio, and the like.

The term "approximately" herein refers to the range of the experimental error, which may occur in a measurement.

The terms "comprising", "having", "including" and "containing" are to be construed as open-ended terms (i.e. meaning "including, but not limited to") and are to be considered as including and/or providing support also for terms as "consist essentially of", "consisting essentially of", "consist of" or "consisting of".

The terms "consist essentially of", "consisting essentially of" are to be construed as a semi-closed terms, meaning that no other ingredients which materially affects the basic and novel characteristics of the invention are included (optional excipients may thus be included).

The terms "consists of", "consisting of" are to be construed as a closed term.

As used herein, the terms "therapeutically effective amount" and "effective amount" refer to an amount sufficient to elicit the desired biological response. In the present invention the desired biological response is to inhibit, reduce or ameliorate the severity, duration, progression, or onset of a disease, disorder or condition, prevent the advancement, recurrence, or progression of a disease, disorder or condition or a symptom associated with a disease, disorder or condition. The precise amount of compound administered to a subject will depend on the mode of administration, the type and severity of the disease, disorder or condition and on the characteristics of the subject, such as general health, age, sex, body weight and tolerance to drugs. The skilled artisan will be able to determine appropriate dosages depending on these and other factors. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, compounds and pharmaceutical compositions described herein can be administered to a subject in a dosage range from between approximately 0.01 to 100 mg/kg body weight/day for therapeutic treatment.

As used herein, the terms "treat", "treatment" and "treating" refer to therapeutic treatments includes the reduction or amelioration of the progression, severity and/or duration of a disease, disorder or condition, or the amelioration of one or more symptoms (specifically, one or more discernible symptoms) of a disease, disorder or condition, resulting from the administration of one or more therapies (e.g., one or more therapeutic agents such as a compound or composition of the invention). In specific embodiments, the therapeutic treatment includes the amelioration of at least one measurable physical parameter of a disease, disorder or condition. In other embodiments the therapeutic treatment includes the inhibition of the progression of a condition, either physically by, e.g., stabilization of a discernible symptom, physiologically by, e.g., stabilization of a physical parameter, or both. In other embodiments the therapeutic treatment includes the reduction or stabilization of a disease, disorder or condition. The term "curative treatment" as used herein refers to a treatment that aims to cure a disease or to improve symptoms associated with a disease.

The term "palliative treatment" as used herein refers to a treatment or therapy that does not aim at curing a disease but rather at providing relief.

The term "adjuvant treatment" as used herein refers to a treatment that is given in addition to the primary, main or initial treatment.

The term "neoadjuvant treatment" as used herein refers to a treatment that is given before a main treatment, with the aim of reducing the size or extent of a tumor, thus reducing the consequences of a more extensive treatment technique that would be required if the tumor wasn't reduced in size or extent.

As described herein, compounds of the invention may optionally be substituted with one or more substituents, such as illustrated generally below, or as exemplified by particular species of the invention. It will be appreciated that the phrase "optionally substituted" is used interchangeably with the phrase "substituted or unsubstituted." In general, the term "substituted", whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. When the term "optionally substituted" precedes a list, said term refers to all of the subsequent substitutable groups in that list. If a substituent radical or structure is not identified or defined as "optionally substituted", the substituent radical or structure is unsubstituted.

Selection of substituents and combinations of substituents envisioned by this invention are those that result in the formation of stable or chemically feasible compounds. The term "stable", as used herein, refers to compounds that are not substantially altered when subjected to conditions to allow for their production, detection, and, specifically, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week. Only those choices and combinations of substituents that result in a stable structure are contemplated. Such choices and combinations will be apparent to those of ordinary skill in the art and may be determined without undue experimentation.

The term "simultaneous, separate or sequential administration" herein refers to administration of the first and second compound at the same time or in such a manner that the two compounds act in the patient's body at the same time or administration of one compound after the other compound in such a manner to provide a therapeutic effect. In some embodiments the compounds are taken with a meal. In other embodiments, the compounds are taken after a meal, such as 30 minutes or 60 minutes after a meal. In some embodiments, one compound is administered to a patient for a time period followed by administration of the other compound.

As used herein, the terms "subject" and "patient" are used interchangeably. The terms "subject" and "patient" refer to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In one embodiment, the subject is a human.

DETAILED DESCRIPTION OF THE INVENTION

Now it has been surprisingly discovered that some cortexolone derivatives have therapeutically interesting anti-tumoral properties, against tumors, preferably epithelial and/or hormone-dependent tumors.

According to the general concept, the invention is represented by the compounds of formula (I)

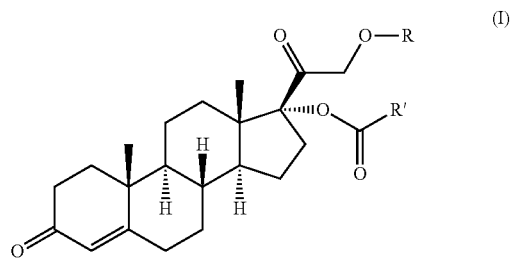

wherein R is hydrogen or C(O)—$R_1$, wherein $R_1$ is a linear alkyl chain containing 2 to 5 carbon atoms, and wherein R' is a linear alkyl chain containing 3 to 6 carbon atoms or an optionally substituted aryl group or an optionally substituted heteroaryl group.

Preferred compounds of formula (I) are those wherein R is hydrogen or C(O)—$R_1$, wherein $R_1$ $CH_2CH_3$ and wherein R' is —$(CH_2)_3$—$CH_3$ or phenyl.

An object of the present invention is represented by the compounds of formula I

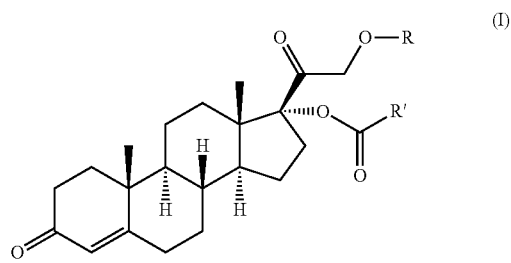

wherein R is C(O)—$R_1$, wherein $R_1$ is hydrogen or a linear alkyl chain containing 2 to 5 carbon atoms, and wherein R' is a linear alkyl chain containing 3 to 6 carbon atoms or an optionally substituted aryl group or an optionally substituted heteroaryl group wherein $R_1$ and R' are not the same.

An object of the present invention is represented by the compounds of formula I

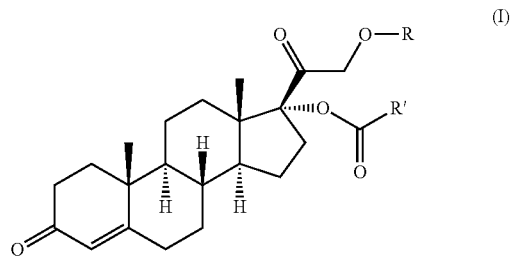

wherein R is C(O)—$R_1$, wherein $R_1$ is a linear alkyl chain containing 2 to 5 carbon atoms, and wherein R' is a linear alkyl chain containing 3 to 6 carbon atoms or an optionally substituted aryl group or an optionally substituted heteroaryl group wherein $R_1$ and R' are not the same.

Preferred compounds of formula (I) are those wherein R is C(O)—R$_1$, wherein R$_1$ is hydrogen or CH$_2$CH$_3$ and wherein R' is —(CH$_2$)$_3$—CH$_3$ or phenyl, wherein R$_1$ and R' are not the same.

Preferred compounds of formula (I) are those wherein R is C(O)—R$_1$, wherein R$_1$ is CH$_2$CH$_3$ and wherein R' is —(CH$_2$)$_3$—CH$_3$ or phenyl, wherein R$_1$ and R' are not the same. The most preferred compound of formula (I) is the compound wherein R is C(O)—R$_1$, wherein R$_1$ is CH$_2$CH$_3$ and wherein R' is —(CH$_2$)$_3$—CH$_3$, that is cortexolone 17α-valerate-21-propionate (herein also referred to as "10" or as "CB-03-10"), whose formula is reported herein below:

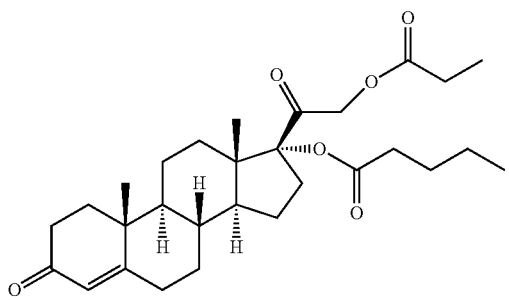

cortexolone 17α-valerato-21-propionate
(Cortexolone 17α-valerate-21-propionate (CB-03-10))

Unless otherwise indicated, structures depicted herein are also meant to include all isomeric (e.g., enantiomeric, diastereomeric, cis-trans, conformational, and rotational) forms of the structure. For example, the R and S configurations for each asymmetric center, (Z) and (E) double bond isomers, and (Z) and (E) conformational isomers are included in this invention, unless only one of the isomers is drawn specifically. As would be understood to one skilled in the art, a substituent can freely rotate around any rotatable bonds. Therefore, single stereochemical isomers as well as enantiomeric, diastereomeric, cis/trans, conformational, and rotational mixtures of the present compounds are within the scope of the invention.

Unless otherwise indicated, all tautomeric forms of the compounds of the invention are within the scope of the invention.

Additionally, unless otherwise indicated, structures depicted herein are also meant to include compounds that differ only in the presence of one or more isotopically enriched atoms.

For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays. Such compounds, especially deuterium analogues, can also be therapeutically useful.

The compounds of the invention are defined herein by their chemical structures and/or chemical names. Where a compound is referred to by both a chemical structure and a chemical name, and the chemical structure and chemical name conflict, the chemical structure is determinative of the compound's identity.

Pharmaceutically Acceptable Salts, Solvates, Clatrates, Prodrugs and Other Derivatives The compounds described herein can exist in free form, or, where appropriate, as salts. Those salts that are pharmaceutically acceptable are of particular interest since they are useful in administering the compounds described below for medical purposes. Salts that are not pharmaceutically acceptable are useful in manufacturing processes, for isolation and purification purposes, and in some instances, for use in separating stereoisomeric forms of the compounds of the invention or intermediates thereof.

As used herein, the term "pharmaceutically acceptable salt" refers to salts of a compound which are, within the scope of sound medical judgment, suitable for use in contact with the tissues of humans and lower animals without undue side effects, such as, toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds described herein include those derived from suitable inorganic and organic acids and bases. These salts can be prepared in situ during the final isolation and purification of the compounds.

It should be understood that this invention includes mixtures/combinations of different pharmaceutically acceptable salts and also mixtures/combinations of compounds in free form and pharmaceutically acceptable salts.

In addition to the compounds described herein, pharmaceutically acceptable solvates (e.g., hydrates) and clathrates of these compounds may also be employed in compositions to treat or prevent the herein identified disorders.

As used herein, the term "pharmaceutically acceptable solvate," is a solvate formed from the association of one or more pharmaceutically acceptable solvent molecules to one of the compounds described herein. The term solvate includes hydrates (e.g., hemihydrate, monohydrate, dihydrate, trihydrate, tetrahydrate, and the like).

As used herein, the term "hydrate" means a compound described herein or a salt thereof that further includes a stoichiometric or non-stoichiometric amount of water bound by non-covalent intermolecular forces.

As used herein, the term "clathrate" means a compound described herein or a salt thereof in the form of a crystal lattice that contains spaces (e.g., channels) that have a guest molecule (e.g., a solvent or water) trapped within.

In addition to the compounds described herein, pharmaceutically acceptable derivatives or prodrugs of these compounds may also be employed in compositions to treat or prevent the herein identified disorders.

A "pharmaceutically acceptable derivative or prodrug" includes any pharmaceutically acceptable ester, salt of an ester or other derivative or salt thereof of a compound described herein which, upon administration to a recipient, is capable of providing, either directly or indirectly, a compound described herein or an inhibitory active metabolite or residue thereof. Particularly favored derivatives or prodrugs are those that increase the bioavailability of the compounds when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds described herein include, without limitation, esters, amino acid esters, phosphate esters, metal salts and sulfonate esters.

Medical Uses

Another object of the present invention is represented by the compounds of formula (I) for use as a medicament.

Another object of the present invention is cortexolone 17α-valerate (herein also referred to as "05" or as "CB-03-05"), represented by:

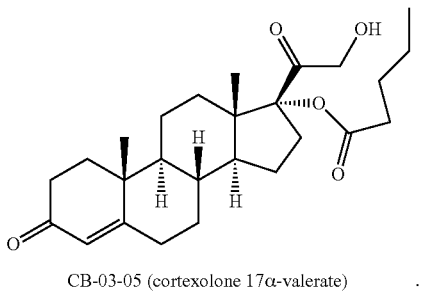

CB-03-05 (cortexolone 17α-valerate)

for use as a medicament.

In one embodiment the compounds of the invention for use as a medicament are Cortexolone 17α-valerate-21-propionate (CB-03-10) and Cortexolone 17α-Valerate (CB-03-05).

In another embodiment the present invention is compositions and pharmaceutical compositions comprising compounds of formula (I) for use as a medicament.

In one embodiment the present invention is compositions and pharmaceutical compositions comprising compounds Cortexolone 17α-valerate-21-propionate (CB-03-10) and Cortexolone 17α-Valerate (CB-03-05) for use as a medicament.

In another aspect, the invention relates to said compounds of formula (I), including Cortexolone 17α-valerate-21-propionate (CB-03-10) and Cortexolone 17α-Valerate (CB-03-05) for use as a Glucocorticoid Receptor (GR) modulator, preferably a glucocorticoid antagonist.

In another embodiment the present invention is compositions and pharmaceutical compositions comprising compounds of formula (I) for use as a Glucocorticoid Receptor (GR) modulator, preferably a glucocorticoid antagonist.

In another embodiment the present invention is compositions and pharmaceutical compositions comprising Cortexolone 17α-valerate-21-propionate (CB-03-10) and Cortexolone 17α-Valerate (CB-03-05) for use as a Glucocorticoid Receptor (GR) modulator, preferably a glucocorticoid antagonist.

In yet another aspect, the invention relates to said compounds of formula (I) for use in treating a disease or disorder mediated by glucocorticoid. In one embodiment the compounds of the invention in treating a disease or disorder mediated by glucocorticoid are Cortexolone 17α-valerate-21-propionate (CB-03-10) and Cortexolone 17α-Valerate (CB-03-05).

In still another aspect, the invention relates to said compounds of formula (I), including Cortexolone 17α-valerate-21-propionate (CB-03-10) and Cortexolone 17α-Valerate (CB-03-05) for use in the treatment of precancerous lesions, dysplasias, metaplasias and tumor diseases, including malignant neoplasias and metastasis; according to another aspect, such a treatment may be curative, adjuvant, neoadjuvant or palliative.

Ideally, the compounds of formula (I), including Cortexolone 17α-valerate-21-propionate (CB-03-10) and Cortexolone 17α-Valerate (CB-03-05) are for use as an anti-tumor agent.

In an embodiment, said tumor diseases are solid tumors, preferably epithelial tumors, such as, by way of example, prostate carcinoma, mammary carcinoma, pancreatic carcinoma, lung carcinoma, gastrointestinal tract carcinoma (preferably colon carcinoma), kidney cancer, thyroid carcinoma, uterine carcinoma and adrenal carcinoma and the like.

In a preferred embodiment of the invention herein disclosed, said epithelial tumors are prostate carcinoma, pancreatic carcinoma (preferably exocrine pancreatic carcinoma), gastrointestinal tract carcinoma (preferably colon carcinoma) and mammary carcinoma (preferably triple negative breast cancer).

In a preferred embodiment of the invention herein disclosed, the tumor diseases are prostate cancer. In a preferred embodiment of the invention herein disclosed, the prostate cancer is an adenocarcinoma. In a preferred embodiment of the invention herein disclosed, the tumor diseases are prostate cancer with absent or reduced expression of AR. In another preferred embodiment of the invention, the tumor diseases are prostate cancer with mutated or truncated Androgen Receptors.

Ideally, the compounds of formula (I), including Cortexolone 17α-valerate-21-propionate (CB-03-10) and Cortexolone 17α-Valerate (CB-03-05) are for use as an anti-tumor agent where the tumor diseases are prostate cancer with mutated or truncated Androgen Receptors. One particularly advantageous use of the compounds of formula (I), including Cortexolone 17α-valerate-21-propionate (CB-03-10) and Cortexolone 17α-Valerate (CB-03-05), is for use in the treatment of prostate cancers that are or have become resistant to anti-androgen treatment, such as enzalutamide. This is a particularly advantageous embodiment of the invention as it has recently been found that after 6 months of treatment 30% of prostate cancers became resistant to enzalutamide because the AR has mutated or changed. Interestingly these resistant cancer cells upregulate the GR. The compounds of formula (I), including Cortexolone 17α-valerate-21-propionate (CB-03-10) and Cortexolone 17α-Valerate (CB-03-05), can be used to treat such cancers as the activity is also mediated through the GR.

In a preferred embodiment of the invention herein disclosed, the exocrine pancreatic carcinoma is an adenocarcinoma. In a preferred embodiment the exocrine pancreatic cancer with absent or reduced expression of the AR.

In a preferred embodiment of the invention herein disclosed, said epithelial tumor is gastrointestinal tract carcinoma (preferably colon carcinoma).

In a still preferred embodiment of the invention herein disclosed, said epithelial tumor is mammary carcinoma (preferably triple negative breast cancer). Optionally, the subject or patient being treated is a non-responder or a relapse to conventional therapy.

In a preferred embodiment, the present invention provides the compounds of formula (I), wherein R is C(O)—$R_1$, wherein $R_1$ is hydrogen or $CH_2CH_3$ and R' is —$(CH_2)_3$—$CH_3$ or a phenyl group, wherein $R_1$ and R' are not the same, for use in the treatment of precancerous lesions, dysplasias, metaplasias and tumor diseases, including malignant neoplasias and metastasis; according to another aspect, such a treatment may be curative, adjuvant, neoadjuvant or palliative. Ideally, the compound is for use as an anti-tumor agent.

In a preferred embodiment, the present invention provides the compounds of formula (I), wherein R is C(O)—$R_1$, wherein $R_1$ is $CH_2CH_3$ and R' is —$(CH_2)_3$—$CH_3$ or a phenyl group, wherein $R_1$ and R' are not the same, for use in the treatment of precancerous lesions, dysplasias, metaplasias and tumor diseases, including malignant neoplasias and metastasis; according to another aspect, such a treatment may be curative, adjuvant, neoadjuvant or palliative. Ideally, the compound is for use as an anti-tumor agent.

In another embodiment, the present invention provides the compound of formula (I) wherein R is C(O)—$R_1$, wherein $R_1$ $CH_2CH_3$ and wherein R' is —$(CH_2)_3$—$CH_3$, that is cortexolone 17α-valerate-21-propionate (herein also referred to as "10" or as "CB-03-10"), for use in the treatment of precancerous lesions, dysplasias, metaplasias and tumor diseases, including malignant neoplasias and metastasis; according to another aspect, such a treatment may be curative, adjuvant, neoadjuvant or palliative. Ideally, the compound is for use as an anti-tumor agent.

In an embodiment, said tumor diseases are solid tumors, preferably epithelial tumors, such as, by way of example, prostate carcinoma, mammary carcinoma, pancreatic carcinoma, lung carcinoma, gastrointestinal tract carcinoma (preferably colon carcinoma), kidney cancer, thyroid carcinoma, uterine carcinoma and adrenal carcinoma and the like.

In a preferred embodiment of the invention herein disclosed, said epithelial tumors are prostate carcinoma, pancreatic carcinoma (preferably exocrine pancreatic carcinoma), gastrointestinal tract carcinoma (preferably colon carcinoma) and mammary carcinoma (preferably triple negative breast cancer).

In a preferred embodiment of the invention herein disclosed, the tumor diseases are prostate cancer. In a preferred embodiment of the invention herein disclosed, the prostate cancer is an adenocarcinoma. In a preferred embodiment of the invention herein disclosed, the tumor diseases are prostate cancer with mutated, absent or reduced expression of the AR.

In a preferred embodiment of the invention herein disclosed, the exocrine pancreatic carcinoma is an adenocarcinoma. In a preferred embodiment the exocrine pancreatic cancer with absent or reduced expression of the AR.

Another object of the present invention is represented by the compounds of formula (I) for use in the manufacture of medicament for the treatment of precancerous lesions, dysplasias, metaplasias and tumor diseases, including malignant neoplasias and metastasis; according to another aspect, such a treatment may be curative, adjuvant, neoadjuvant or palliative. In one embodiment the compounds of the invention are for use in the manufacture of a medicament for the treatment of precancerous lesions, dysplasias, metaplasias and tumor diseases, including malignant neoplasias and metastasis are Cortexolone 17α-valerate-21-propionate (CB-03-10) and Cortexolone 17α-Valerate (CB-03-05). Ideally, the compounds of formula (I) are for use in the manufacture of an anti-tumor agent. In one embodiment the compounds of the invention for use in the manufacture of anti tumor agents are Cortexolone 17α-valerate-21-propionate (CB-03-10) and Cortexolone 17α-Valerate (CB-03-05).

In an embodiment, said tumor diseases are solid tumors, preferably epithelial tumors, such as, by way of example, prostate carcinoma, mammary carcinoma, pancreatic carcinoma, lung carcinoma, gastrointestinal tract carcinoma (preferably colon carcinoma), kidney cancer, thyroid carcinoma, uterine carcinoma and adrenal carcinoma and the like.

In another aspect, the invention relates to said compounds of formula (I) for use in the manufacture of a medicament for treating a disease or disorder mediated by glucocorticoid.

In one aspect, the invention herein disclosed provides a method for treating precancerous lesions, dysplasias, metaplasias and tumor diseases, including malignant neoplasias and metastasis, said method comprising the administration of an effective amount of a compound of formula (I):

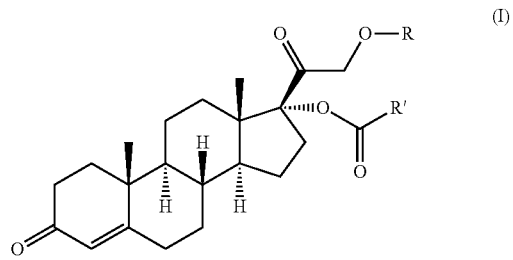

wherein R is C(O)—$R_1$, wherein $R_1$ is hydrogen or a linear alkyl chain containing 2 to 5 carbon atoms, and wherein R' is a linear alkyl chain containing 3 to 6 carbon atoms or an optionally substituted aryl group or an optionally substituted heteroaryl group, wherein $R_1$ and R' are not the same, to a subject in need thereof. Preferably, said subject is a mammal. Preferably, said mammal is a human.

In one aspect, the invention herein disclosed provides a method for treating precancerous lesions, dysplasias, metaplasias and tumor diseases, including malignant neoplasias and metastasis, said method comprising the administration of an effective amount of a compound of formula (I):

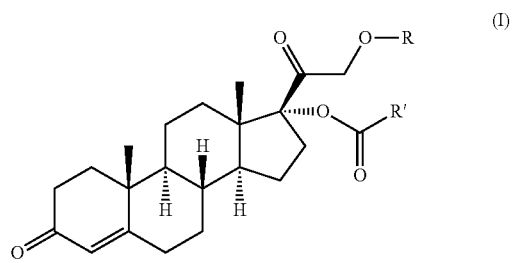

wherein R is C(O)—$R_1$, wherein $R_1$ is a linear alkyl chain containing 2 to 5 carbon atoms, and wherein R' is a linear alkyl chain containing 3 to 6 carbon atoms or an optionally substituted aryl group or an optionally substituted heteroaryl group, wherein $R_1$ and R' are not the same, to a subject in need thereof. Preferably, said subject is a mammal. Preferably, said mammal is a human.

In an embodiment, said tumor diseases are solid tumors, particularly epithelial tumors, such as, by way of example, prostate carcinoma, mammary carcinoma, uterine carcinoma, pancreatic carcinoma, lung carcinoma, gastro-intestinal tract carcinoma (preferably colon carcinoma), kidney cancer, thyroid carcinoma, and adrenal carcinoma and the like.

In an embodiment, said tumor diseases are solid tumors, particularly epithelial tumors, such as, by way of example, prostate carcinoma, mammary carcinoma, uterine carcinoma, pancreatic carcinoma, lung carcinoma, gastro-intestinal tract carcinoma (preferably colon carcinoma), kidney cancer, thyroid carcinoma, uterine carcinoma and adrenal carcinoma and the like.

In a preferred embodiment of the invention herein disclosed, said epithelial tumors are prostate carcinoma or pancreatic carcinoma, more preferably exocrine pancreatic carcinoma, or mammary carcinoma, such as, triple negative breast cancer. In a preferred embodiment of the invention herein disclosed, the tumor diseases are prostate cancer with absent or reduced expression of AR. In another preferred embodiment of the invention, the tumor diseases are prostate cancer with mutated or truncated Androgen Receptors. In this manner, the prostate cancer that may be treated according to the invention may be or have become resistant to anti-androgen targeted therapy, such as enzalutamide.

According to a preferred embodiment, said method comprises the administration of an effective amount of a compound of formula (I) wherein R is C(O)—$R_1$, wherein $R_1$ is hydrogen or $CH_2CH_3$ and R' is —$(CH_2)_3$—$CH_3$ or a phenyl group wherein $R_1$ and R' are not the same, to a mammal in need thereof.

According to a preferred embodiment, said method comprises the administration of an effective amount of a compound of formula (I) wherein R is C(O)—$R_1$, wherein $R_1$ is $CH_2CH_3$ and R' is —$(CH_2)_3$—$CH_3$ or a phenyl group wherein $R_1$ and R' are not the same, to a mammal in need thereof. In a most preferred embodiment, said method comprises the administration of an effective amount of a compound of formula (I) wherein R is C(O)—$R_1$, $R_1$ is $CH_2CH_3$ and R' is —$(CH_2)_3$—$CH_3$, that is cortexolone 17α-valerate-21-propionate (CB-03-10).

In one aspect, the invention herein disclosed provides a method for treating precancerous lesions, dysplasias, metaplasias and tumor diseases, including malignant neoplasias and metastasis, said method comprising the administration of an effective amount of cortexolone 17α-valerate (CB-03-05), to a subject in need thereof. Preferably, said subject is a mammal. Preferably, said mammal is a human.

In an embodiment, said tumor diseases are solid tumors, particularly epithelial tumors, such as, by way of example, prostate carcinoma, mammary carcinoma, uterine carcinoma, pancreatic carcinoma, lung carcinoma, gastro-intestinal tract carcinoma (preferably colon carcinoma), kidney cancer, thyroid carcinoma, and adrenal carcinoma and the like.

In a preferred embodiment of the invention herein disclosed, said epithelial tumors are prostate carcinoma or pancreatic carcinoma, more preferably exocrine pancreatic carcinoma, or mammary carcinoma, such as, triple negative breast cancer. The compounds of the present invention can be used in different therapeutic applications, especially oncologic applications. More in details, the compounds according to the invention herein disclosed have been found particularly effective for the curative or adjuvant, or neoadjuvant or palliative treatment of pancreatic carcinoma, preferably exocrine pancreatic carcinoma, and prostatic carcinoma. An illustration of the pharmacological properties of the compounds of the invention will be found hereafter in the experimental section.

The compounds of formula (I) may be prepared according to any conventional method, for instance by the processes disclosed in WO03/014141 and in WO2009/019138, the contents of each of which are herein incorporated by reference their entireties. According to an embodiment of the invention, cortexolone 17α-valerate-21-propionate (CB-03-10) and cortexolone 17α-valerate (CB-03-05) can be prepared according to the method disclosed in example 11.

Pharmaceutical Compositions

The compounds described herein can be formulated into pharmaceutical compositions that further comprise a pharmaceutically acceptable carrier, diluent, adjuvant or vehicle. In one embodiment, the present invention relates to a pharmaceutical composition comprising a compound of the invention described herein, and a pharmaceutically acceptable carrier, diluent, adjuvant or vehicle. In one embodiment, the present invention is a pharmaceutical composition comprising an effective amount of a compound of the present invention or a pharmaceutically acceptable salt thereof and a pharmaceutically acceptable carrier, diluent, adjuvant or vehicle. Pharmaceutically acceptable carriers include, for example, pharmaceutical diluents, excipients or carriers suitably selected with respect to the intended form of administration, and consistent with conventional pharmaceutical practices.

Another object of the present invention is represented by a pharmaceutical composition comprising, as active ingredient, at least one compound of formula (I), wherein R is —C(O)—$R_1$, wherein $R_1$ is hydrogen or a linear alkyl chain containing 2 to 5 carbon atoms, and wherein R' is a linear alkyl chain containing 3 to 6 carbon atoms or an optionally substituted aryl group or an optionally substituted heteroaryl group, wherein $R_1$ and R' are not the same in association with at least one physiologically acceptable excipient.

Another object of the present invention is represented by a pharmaceutical composition comprising, as active ingredient, at least one compound of formula (I), wherein R is C(O)—$R_1$, wherein $R_1$ is a linear alkyl chain containing 2 to 5 carbon atoms, and wherein R' is a linear alkyl chain containing 3 to 6 carbon atoms or an optionally substituted aryl group or an optionally substituted heteroaryl group, wherein $R_1$ and R' are not the same in association with at least one physiologically acceptable excipient. According to a preferred embodiment of the invention said pharmaceutical composition comprises, as active ingredient, at least one compound of formula (I) wherein R is C(O)—$R_1$, wherein $R_1$ is hydrogen or —$CH_2CH_3$ and R' is —$(CH_2)_3$—$CH_3$ or a phenyl group, wherein $R_1$ and R' are not the same.

According to a preferred embodiment of the invention said pharmaceutical composition comprises, as active ingredient, at least one compound of formula (I) wherein R is C(O)—$R_1$, wherein $R_1$ is $CH_2CH_3$ and R' is —$(CH_2)_3$—$CH_3$ or a phenyl group, wherein $R_1$ and R' are not the same. According to a most preferred embodiment, said pharmaceutical composition comprises, as active ingredient, cortexolone 17α-valerate-21-propionate (CB-03-10), in association with at least one physiologically acceptable excipient. Another object of the present invention is represented by a pharmaceutical composition comprising, as active ingredient, cortexolone 17α-valerate (CB-03-05) in association with at least one physiologically acceptable excipient.

In a further object, the compounds and pharmaceutical compositions of the invention are for use as a medicament, preferably in the treatment of precancerous lesions, dysplasias, metaplasias and tumor diseases, including malignant neoplasias and metastasis; according to another aspect, such a treatment may be curative, adjuvant, neoadjuvant or palliative. In this manner, they are used as anti-tumor agents. Preferably, said tumor diseases are solid tumors. More preferably, said solid tumors are epithelial tumors, such as, by way of example, prostate carcinoma, mammary carcinoma, pancreatic carcinoma, lung carcinoma, gastro-intestinal tract carcinoma (preferably colon carcinoma), kidney cancer, thyroid carcinoma, uterine carcinoma and adrenal carcinoma and the like. In a preferred embodiment of the invention herein disclosed, said epithelial tumors are prostate carcinoma and pancreatic carcinoma, more preferably exocrine pancreatic carcinoma or mammary carcinoma, such as, triple negative breast cancer. In another preferred embodiment of the invention, the tumor diseases are prostate cancer with mutated or truncated Androgen Receptors. Ideally, the pharmaceutical compositions comprising compounds of formula (I), including Cortexolone 17α-valerate-21-propionate (CB-03-10) and Cortexolone 17α-Valerate (CB-03-05), for use as an anti-tumor agent where the tumor diseases are prostate cancer with mutated or truncated Androgen Receptors. In this manner, the prostate cancer that may be treated according to the invention may be or have become resistant to anti-androgen targeted therapy, such as enzalutamide.

As described above, in another embodiment, there is provided pharmaceutical compositions comprising compounds of formula (I), including Cortexolone 17α-valerate-21-propionate (CB-03-10) and Cortexolone 17α-Valerate (CB-03-05), for use as a Glucocorticoid Receptor (GR) modulator, preferably a glucocorticoid antagonist.

The pharmaceutical compositions of the invention can be in solid form, such as, by way of example, powders, freeze-dried powders, granules, pellets, tablets or capsules. If desired, certain sweetening, flavoring or coloring agents may also be added. The compounds of the invention can also be in microencapsulated form with one or more excipients. The solid dosage forms of tablets, capsules, pills, and granules can be prepared with coatings and shells such as enteric coatings and other coatings well known in the pharmaceutical formulating art. Appropriate excipients for solid pharmaceutical compositions can be selected, without any limitation, among the categories known to a person skilled in the art such as adsorbents, fillers, surfactants, compression aids, binders, lubricants, disintegrants, diluents, disgregants, flow promoting agents, freeze-drying agents, glidants, lyophilization aids, film-forming agents, dyes, antioxidants, and the like. By way of example, suitable excipients for solid pharmaceutical compositions can be selected, in a non-limiting way, from calcium phosphate, magnesium stearate, talc, sugars, lactose, dextrin, starch, gelatin, cellulose and derivatives thereof, polyvinylpyrrolidone, coating agents, dyes and wax. Any mixture of these excipients can be properly used according to the invention.

According to the invention, solid pharmaceutical compositions such as tablets, granules, pellets, capsules and the like, can be formulated as immediate release forms or as delayed release forms or as controlled release forms or as extended release forms or as prolonged release forms, and are suitable for administration by the oral, or sublingual administration route or as an implant.

The controlled, extended and/or prolonged composition may be prepared according to to any conventional method or system, for instance according to WO00/76478 herein incorporated by reference in it's entirety.

The pharmaceutical compositions of the invention can also be in liquid form, for example, solutions, emulsions, suspensions or syrups. Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art. Besides inert diluents, the oral compositions can also include adjuvants such as wetting agents, emulsifying and suspending agents, sweetening, flavoring, and perfuming agents. Appropriate excipients for liquid pharmaceutical composition can be selected, without any limitation, among the categories well known to a person skilled in the art, such as solvents, co-solvents, oleaginous vehicles, buffering agents, surfactants, emulsifying agents, solubility enhancing agents, suspending agents, solubilizing agents, chelating agents, acidifying agents, alkalinizing agents, antioxidants, preservatives, osmotic agents, tonicity agents, viscosity controlling agents and the like. By way of example, suitable pharmaceutical excipients for liquid preparation can be selected from water for injections, organic solvents or co-solvents such as ethanol, glycols and glycerol and mixtures thereof, natural oils such as soybean oil, medium-chain triglycerides, polyoxyl 15-hydroxystearate, polysorbate 80, polyoxyl 35-castor oil, sodium chloride, sodium phosphate, potassium phosphate, and the like. According to the invention, said liquid pharmaceutical compositions can be sterile or non-sterile. In one embodiment, the liquid pharmaceutical compositions are terminally sterilized by means of a technique well known to a person skilled in the art, such as dry heat sterilization, moist heat sterilization, gamma radiation, e-beam sterilization and the like. In another embodiment, the liquid pharmaceutical compositions are sterilized by sterile filtration and aseptically filled in the final primary packaging containers. The liquid pharmaceutical compositions according to the invention herein disclosed can be used for injections, infusions or perfusions such as intravenous, intramuscular, intraperitoneal, subcutaneous or intratumoral administration.

Administration Methods

The compounds and compositions described herein may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrastemal, intrathecal, intrahepatic, intralesional and intracranial injection or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Sterile injectable forms of the compounds and compositions described herein may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally-acceptable diluent or solvent.

The compounds for use in the methods of the invention can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose.

According to the invention, the compounds of formula (I) or the pharmaceutical compositions comprising the said compounds are preferably administered by intravenous injection, more preferably through an infusion bag or a syringe or a pump catheter, or by intramuscular injection, or by subcutaneous injection, or per os (by mouth) in forms of tablets or capsules.

According to an embodiment, said pharmaceutical composition is in liquid form and is suitable for injection, and comprise a cortexolone-derived compound of formula (I) in an amount ranging from 0.1% to 50.0% weight to volume (w/v), preferably from 0.25% to 25% w/v, more preferably from 0.5% to 10% w/v, much more preferably from 1% to 5% w/v.

According to another embodiment, said pharmaceutical composition is in solid form and comprises a cortexolone-derived compound of formula (I) in an amount ranging from 0.1% to 50% weight to weight (w/w), preferably from 0.5% to 40% w/w, more preferably from 1% to 30% w/w.

The amount of the at least one compound of formula (I) in said pharmaceutical composition is such that an effective dosage level can be obtained upon administration to a mammal suffering of precancerous lesions, dysplasias, metaplasias and tumor diseases, including malignant neoplasias and metastasis. The compounds of formula (I) and the pharmaceutical composition comprising the same as antitumor active ingredients for use in the curative or adjuvant, or neoadjuvant or palliative treatment of precancerous lesions, dysplasias, metaplasias and tumor diseases, including malignant neoplasias and metastasis, are preferably administered to a mammal, said mammal being a human or an animal, preferably a human.

Combination Therapy

According to another embodiment, the compounds, compositions and pharmaceutical compositions may contain at least another active ingredient, preferably a chemotherapeutic active ingredient, as a combination for simultaneous, separate or sequential administration.

In certain embodiments, the compounds of formula (I) and the pharmaceutical composition comprising at least one compound of formula (I) and at least one physiologically acceptable excipient according to the invention can be used in combination therapy with at least one other drug, especially a chemotherapeutic drug.

In certain embodiments, the compounds of the invention can be administered concurrently with the administration of another drug, especially a chemotherapeutic drug. In certain embodiments, the compounds of the invention can be administered prior to or subsequent to administration of another drug, especially a chemotherapeutic drug. Said at least one other drug, especially a chemotherapeutic drug, can be effective for treating the same or different disease, disorder, or condition.

Methods of the present invention include administration of one or more compounds of formula (I) or pharmaceutical compositions comprising at least a compound of formula (I) of the present invention and at least another drug, preferably a chemotherapeutic drug, provided that the combined administration does not inhibit the therapeutic efficacy of the one or more compounds of the present invention and/or does not produce non-acceptable adverse combination effects.

Cortexolone 17α-Valerate (Herein Also Referred to as "05" or as "CB-03-05")

As described above, another object of the present invention is cortexolone 17α-valerate (herein also referred to as "05" or as "CB-03-05"), represented by:

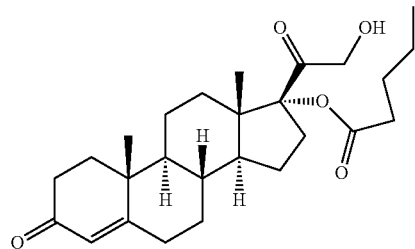

CB-03-05 (cortexolone 17α-valerate)

for use as a medicament.

Ideally, cortexolone 17α-valerate is for use in the treatment of precancerous lesions, dysplasias, metaplasias and tumor diseases, optionally including malignant neoplasias and metastasis. Preferably, cortexolone 17α-valerate is for use as an anti-tumor agent.

Preferably, the tumor diseases are solid tumors, preferably epithelial tumors. The epithelial tumors may be selected from prostate carcinoma; mammary carcinoma; pancreatic carcinoma (preferably exocrine pancreatic cancer); lung carcinoma; gastrointestinal tract carcinoma, such as colon carcinoma; kidney cancer; thyroid carcinoma; uterine carcinoma; and adrenal carcinoma.

According to one embodiment, the epithelial tumor is a prostate carcinoma. In another preferred embodiment of the invention, the tumor diseases are prostate cancer with mutated or truncated Androgen Receptors. In this manner, the prostate cancer that may be treated according to the invention may be or have become resistant to anti-androgen targeted therapy, such as enzalutamide.

According to another embodiment, the epithelial tumors are pancreatic carcinoma, preferably exocrine pancreatic carcinoma.

According to one embodiment, the epithelial tumors are mammary carcinoma, preferably triple negative breast cancer (TNBC). In one embodiment, the mammary carcinoma is triple negative breast cancer and the subject is a relapsed or a non-responder to conventional therapy.

According to another embodiment, the epithelial tumors are gastrointestinal tract carcinoma, such as colon carcinoma.

According to another embodiment, cortexolone 17α-valerate is for use as a Glucocorticoid Receptor (GR) modulator, preferably a glucocorticoid antagonist.

According to another aspect, there is provided a pharmaceutical composition comprising a compound of the following structural formula:

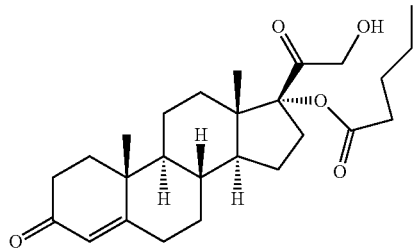

and at least one physiologically acceptable excipient for use as a medicament, preferably in the treatment of precancerous lesions, dysplasias, metaplasias and tumor diseases, optionally including malignant neoplasias and metastasis. Preferably said tumor diseases are solid tumors, preferably epithelial tumors, such as prostate carcinoma; mammary carcinoma; pancreatic carcinoma; lung carcinoma; gastrointestinal tract carcinoma, such as colon carcinoma; kidney cancer; thyroid carcinoma; uterine carcinoma; adrenal carcinoma.

According to another embodiment, said epithelial tumor is prostate carcinoma. In another preferred embodiment of the invention, the tumor diseases are prostate cancer with mutated or truncated Androgen Receptors. In this manner, the prostate cancer that may be treated according to the invention may be or have become resistant to anti-androgen targeted therapy, such as enzalutamide.

According to another embodiment, the epithelial tumors are pancreatic carcinoma, preferably exocrine pancreatic carcinoma.

According to another embodiment, the epithelial tumors are mammary carcinoma, preferably triple negative breast cancer (TNBC). In one embodiment, the mammary carcinoma is triple negative breast cancer and the subject is a relapsed or a non-responder to conventional therapy.

According to another embodiment, the epithelial tumors are gastrointestinal tract carcinoma, such as colon carcinoma.

The pharmaceutical composition may also comprise at least one other active ingredient, preferably a chemotherapeutic active ingredient, for simultaneous, separate or sequential administration.

According to another aspect, there is provided a pharmaceutical composition comprising a compound of the following structural formula:

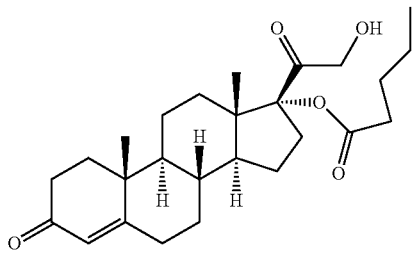

and at least one physiologically acceptable excipient for use as a Glucocorticoid Receptor (GR) modulator, preferably a glucocorticoid antagonist.

In another aspect, there is provided a method of treating precancerous lesions, dysplasias, metaplasias and tumor diseases in a subject in need thereof, comprising administrating a therapeutically effective amount of a compound of the following structural formula:

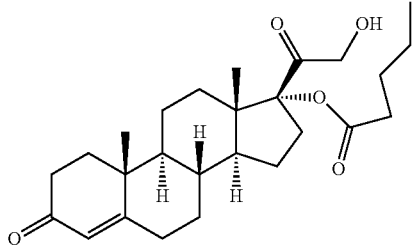

or a pharmaceutical composition comprising said compound to said subject.

According to one embodiment, the tumor diseases are malignant neoplasias or metastasis.

Preferably, the subject is a mammal. Ideally, the mammal is a human.

According to one embodiment, the tumor diseases are solid tumors. Optionally, the solid tumors are epithelial tumors. The epithelial tumors may be selected from prostate carcinoma, mammary carcinoma, uterine carcinoma, pancreatic carcinoma, lung carcinoma, gastro-intestinal tract carcinoma (preferably colon carcinoma), kidney cancer, thyroid carcinoma, uterine carcinoma and adrenal carcinoma and the like.

According to another embodiment, the epithelial tumors are prostate carcinoma, pancreatic carcinoma, exocrine pancreatic carcinoma, or mammary carcinoma.

According to another embodiment, said epithelial tumor is prostate carcinoma. In another preferred embodiment of the invention, the tumor diseases are prostate cancer with mutated or truncated Androgen Receptors. In this manner, the prostate cancer that may be treated according to the invention may be or have become resistant to anti-androgen targeted therapy, such as enzalutamide.

According to another embodiment, the epithelial tumors are pancreatic carcinoma, preferably exocrine pancreatic carcinoma.

According to another embodiment, wherein the mammary carcinoma is triple negative breast cancer. In one embodiment, the mammary carcinoma is triple negative breast cancer and the subject is a relapsed or a non-responder to conventional therapy.

According to another embodiment, the epithelial tumors are gastrointestinal tract carcinoma, such as colon carcinoma.

According to another aspect of the invention, there is provided a method of treating a disease or disorder mediated by glucocorticoid, in a subject in need thereof, the method comprising administrating a therapeutically effective amount of cortexolone 17α-valerate or a pharmaceutical composition comprising cortexolone 17α-valerate.

EXAMPLES

Example 1: In-Vitro Antitumor Activity of Cortexolone 17α-Benzoate (CB-03-06) on Prostate Cancer Cell Lines The experiment was performed to test and to define the antitumor activity in vitro of cortexolone 17α-benzoate on LNCaP (AR$^+$) and PC3 (AR$^-$), representative of Prostatic cancer cell lines with Androgen Receptor (AR) positive or negative expression, respectively. The experimental method consisted of:

1. 3000 cancer cells were seeded in 96-well flat bottom plates in complete media containing 2% charcoal stripped bovine serum. 2. After 24 hours, 10 nM DHT (dihydrotestosterone) with or without anti-androgen compounds, or DMSO vehicle (negative control) was added to the cultures.
3. After 3 days, viable cell numbers were quantitated using an ATP-dependent proliferation assay.

The aim of the test was to determine the concentration at which each compound kills 50% of the cancer cells ($IC_{50}$) in view of a potential application of the compound in in vivo animal test.

Data from Experiment 1 was fitted through sigmoidal dose response curves and analyzed using Prizm statistical analysis software. Data from Experiment 2 were analyzed using nonlinear regression least squares curve fit in Prizm statistical analysis software.

The $IC_{50}$ value found for each line is reported in the following table, compared to well known comparators the most potent anti-androgenic steroid, CPA, and Enzalutamide, an oral Androgen Receptor inhibitor able to prolong survival in men with metastatic castration-resistant prostate cancer currently used to treat prostate cancer. The results from 2 sets of experiments follow.

Experiment 1

The results were fitted through sigmoidal dose response curves in Prizm statistical analysis software.

| Tumour Cell lines | IC$_{50}$ (microM) CB-03-06 [Cortexolone 17α-benzoate] | IC$_{50}$ (microM) Cyproterone Acetate IC$_{50}$ | IC$_{50}$ (microM) Enzalutamide |
| --- | --- | --- | --- |
| LNCaP | 12 | 29 | 40 |
| PC 3 | 29 | 98 | 208 |

IC$_{50}$ values show that the antitumor activity of Cortexolone 17α-benzoate, even though with a weak correlation trend, could be considered not strictly dependent on the Androgen Receptor expression, differently from the comparators.

Experiment 2

The results below include additional experiments to those in Experiment 1. The results were analyzed using nonlinear regression least squares curve fit in Prizm statistical analysis software.

| Tumor Cell lines | IC$_{50}$ (microM) CB-03-06 [Cortexolone 17α-benzoate] | IC$_{50}$ (microM) Cyproterone Acetate IC$_{50}$ | IC$_{50}$ (microM) Enzalutamide |
| --- | --- | --- | --- |
| LNCaP | 12 | 22 | 38 |
| PC3 | 28 | 90 | 180 |

Example 2: In-Vitro Antitumor Activity of Cortexolone 17α-Valerate-21-Propionate (CB-03-10) on Prostate Cancer Cell Lines The experiment was performed to test and to define antitumor activity in vitro of cortexolone 17α-valerate-21-propionate (CB-03-10) on LNCaP (AR$^+$) and PC3 (AR$^-$), representative of Prostatic cancer cell lines with AR positive or negative expression, respectively. The experimental method consisted of:

1. 3000 cancer cells were seeded in 96-well flat bottom plates in complete media containing 2% charcoal stripped bovine serum.
2. After 24 hours, 10 nM DHT (dihydrotestosterone) with or without anti-androgen compounds, or DMSO vehicle (negative control) was added to the cultures.
3. After 3 days, viable cell numbers were quantitated using an ATP-dependent proliferation assay.

The aim of the test was to determine the concentration at which each compound kills 50% of the cancer cells (IC$_{50}$) in view of a potential application of the compound in in vivo animal test.

Data from Experiment 1 was fitted through sigmoidal dose response curves and analyzed using Prizm statistical analysis software. Data from Experiment 2 was analyzed using nonlinear regression least squares curve fit in Prizm statistical analysis software.

The IC$_{50}$ value found for each line is reported in the following table, compared to well known comparators: the most potent anti-androgenic steroid, CPA, and Enzalutamide, an oral AR antagonist able to prolong survival in men with metastatic castration-resistant prostate cancer.

Experiment 1

The results were fitted through sigmoidal dose response curves in Prizm statistical analysis software.

| Tumor Cell lines | IC$_{50}$ (microM) CB-03-10 [Cortexolone 17α-valerate-21-propionate] | IC$_{50}$ (microM) Cyproterone Acetate IC$_{50}$ | IC$_{50}$ (microM) Enzalutamide |
| --- | --- | --- | --- |
| LNCaP | 13 | 29 | 40 |
| PC 3 | 55 | 98 | 208 |

Experiment 2

The results below include additional experiments to those in Experiment 1. The results were analyzed using nonlinear regression least squares curve fit in Prizm statistical analysis software.

| Tumor Cell lines | IC$_{50}$ (microM) CB-03-10 [Cortexolone 17α-valerate-21-propionate] | IC$_{50}$ (microM) Cyproterone Acetate IC$_{50}$ | IC$_{50}$ (microM) Enzalutamide |
| --- | --- | --- | --- |
| LNCaP | 10 | 22 | 38 |
| PC 3 | 50 | 90 | 180 |

IC$_{50}$ values show that the antitumor activity of cortexolone 17α-valerate-21-propionate (CB-03-10) could correlate with the Androgen Receptor expression in the cell lines.

Example 3: In-Vitro Antitumor Activity of Cortexolone 17α-Benzoate (CB-03-06) on Pancreatic Cancer Cell Lines The experiment was performed to test and to define the antitumor activity in vitro of cortexolone 17α-benzoate on two pancreatic tumor cell lines, Panc1 (AR$^+$) and MiaPaca2 (AR low), representative of Pancreatic cancer cell lines.

The lines were also classified as positive (AR$^+$) or negative/low (AR$^{+/-}$) for the presence and expression of the Androgen Receptor.

The experimental method consisted of:

1. 3000 cancer cells were seeded in 96-well flat bottom plates in complete media containing 2% charcoal stripped bovine serum
2. After 24 hours, 10 nM DHT (dihydrotestosterone) with or without anti-androgen compounds, or DMSO vehicle (negative control) was added to the cultures.
3. After 3 days, viable cell numbers were quantitated using an ATP-dependent proliferation assay.

The aim of the test was to determine the concentration at which each compound kills 50% of the cancer cells (IC$_{50}$) in view of a potential application of the compound in in vivo animal test.

Data from Experiment 1 were fitted through sigmoidal dose response curves and analyzed using Prizm statistical analysis software. Data from Experiment 2 were analyzed using nonlinear regression least squares curve fit in Prizm statistical analysis software.

The IC$_{50}$ value found for each line is reported in the following table, compared to well known comparators the most potent anti-androgenic steroid, CPA, and Enzalutamide, a potent oral AR antagonist Experiment 1

The results were fitted through sigmoidal dose response curves in Prizm statistical analysis software.

| Tumor Cell lines | $IC_{50}$ (microM) CB-03-06 [Cortexolone 17α-benzoate] | $IC_{50}$ (microM) Cyproterone Acetate $IC_{50}$ | $IC_{50}$ (microM) Enzalutamide |
|---|---|---|---|
| Panc1 | 30 | 54 | 156 |
| MiaPaca2 | 23 | 46 | 77 |

Experiment 2

The results below include additional experiments to those in Experiment 1. The results were analyzed using nonlinear regression least squares curve fit in Prizm statistical analysis software.

| Tumor Cell lines | $IC_{50}$ (microM) CB-03-06 [Cortexolone 17α-benzoate] | $IC_{50}$ (microM) Cyproterone Acetate $IC_{50}$ | $IC_{50}$ (microM) Enzalutamide |
|---|---|---|---|
| Panc1 | 28 | 46 | 111 |
| MiaPaca2 | 20 | 39 | 65 |

$IC_{50}$ values show that the antitumor activity of cortexolone 17α-benzoate is at least twice higher than the activity of the comparators (CPA and Enzalutamide). Since MiaPaca2 are characterized by a low/null AR expression, the anti-cancer activity of the compound is not directly correlated to the Androgen Receptor expression in the cancer cell lines.

Example 4: In Vitro Antitumor Activity of Cortexolone 17α-Valerate-21-Propionate (CB-03-10) on Pancreatic Cancer Cell Lines The experiment was performed to test and to define the antitumor activity in vitro of cortexolone 17α-valerate-21-propionate (CB-03-10) on cell lines representatives of pancreatic tumors, namely Panc1 (AR+) and MiaPaca2 (AR low), representative of Pancreatic cancer cell lines.

The lines were also classified as positive (AR+) or negative/low (AR+/−) for the presence and expression of the Androgen Receptor.

The experimental method consisted of:
1. 3000 cancer cells were seeded in 96-well flat bottom plates in complete media containing 2% charcoal stripped bovine serum
2. After 24 hours, 10 nM DHT (dihydrotestosterone) with or without anti-androgen compounds, or DMSO vehicle (negative control) was added to the cultures.
3. After 3 days, viable cell numbers were quantitated using an ATP-dependent proliferation assay.

The aim of the test was to determine the concentration at which each compound kills 50% of the cancer cells ($IC_{50}$) in view of a potential application of the compound in in vivo animal test.

Data from Experiment 1 were fitted through sigmoidal dose response curves and analyzed using Prizm statistical analysis software. Data from Experiment 2 were analyzed using nonlinear regression least squares curve fit in Prizm statistical analysis software.

The $IC_{50}$ value found for each line is reported in the following table, compared to well known comparators: the most potent anti-androgenic steroid, CPA, and Enzalutamide, an oral AR antagonist.

Experiment 1

The results were fitted through sigmoidal dose response curves in Prizm statistical analysis software.

| Tumor Cell lines | $IC_{50}$ (microM) CB-03-10 [Cortexolone 17α-valerate-21-propionate] | $IC_{50}$ (microM) Cyproterone Acetate $IC_{50}$ | $IC_{50}$ (microM) Enzalutamide |
|---|---|---|---|
| Panc1 | 66 | 54 | 156 |
| MiaPaca2 | 43 | 46 | 77 |

Experiment 2

The results below include additional experiments to those in Experiment 1. The results were analyzed using nonlinear regression least squares curve fit in Prizm statistical analysis software.

| Tumor Cell lines | $IC_{50}$ (microM) CB-03-10 [Cortexolone 17α-valerate-21-propionate] | $IC_{50}$ (microM) Cyproterone Acetate $IC_{50}$ | $IC_{50}$ (microM) Enzalutamide |
|---|---|---|---|
| Panc1 | 60 | 46 | 111 |
| MiaPaca2 | 37 | 39 | 65 |

$IC_{50}$ values show that the antitumor activity of Cortexolone 17α-valerate-21-propionate (CB-03-10) is not correlated with the Androgen Receptor expression on the pancreatic cancer cell lines.

Example 5: In-Vivo Human Pancreatic Tumor Xenograft in Mice

The activity of cortexolone 17α-benzoate (CB-03-06) on pancreatic xenograft tumor growth in nude male mice has been evaluated in comparison with the most potent anti-androgenic steroid Cyproterone Acetate (CPA).

Cortexolone 17α-benzoate and Cyproterone Acetate were separately diluted in DMSO/2-hydroxypropyl β-cyclodextrin (vehicle).

The test was carried out comparing the anti-tumor activity of cortexolone 17α-benzoate at two different dosages (8.0 mg/kg, corresponding approximately at 230 μM, and 40 mg/kg, corresponding approximately at 1150 μM), versus the vehicle (i.e. 0.4% (v/v) tween 80 and 0.5% (w/v) carboxymethylcellulose in normal saline) and versus the comparator Cyproterone Acetate at two different dosages (7.4 mg/kg and 37 mg/kg).

$1 \times 10^6$ MiaPaca-2 cells suspended in matrigel were subcutaneously injected into 6 week old athymic nude mice.

The treatment with the tested compounds, with the vehicle and with the comparative compound, was initiated after the tumor volume has reached 50 mm$^3$ after transplantation. All compounds were injected 100 μL/mouse subcutaneously of low dose solution (approximately 230 μM) or 100 μL/mouse of high dose solution (approximately 1150 μM) of cortexolone 17α-benzoate, vehicle and cyproterone acetate, respectively. Compounds and controls were administered subcutaneously daily for 28 days.

Tumors were measured every 4 days with a digital caliper.

The results are plotted in FIG. 1 as average change in tumor volume relative to the start of treatment. Tumor volume was calculated according to the formula $0.5236(r_1)^2(r_2)$ where $r_1 < r_2$.

Error bars are the SEM for 7 to 10 mice per treatment group. P values were calculated according to the Student's t test.

The high dose of Cortexolone 17α-benzoate maintained the pancreatic tumor size increase of less than 5-fold of the size of the tumor when treatment was initiated. In contrast, the average tumor in the vehicle and in the Cyproterone Acetate treatment groups increased in size to 12-fold. From these data the anti-tumoral activity of the compound of the present invention, cortexolone 17α-benzoate, is evident.

Example 6—In-Vivo Human Pancreatic Tumor Xenograft in Mice

The activity of cortexolone 17α-valerate-21-propionate (CB-03-10) on xenograft model of pancreatic tumor in nude male mice has been evaluated in comparison with the anti-androgenic steroid Cyproterone Acetate (CPA).

Cortexolone 17α-valerate-21-propionate (CB-03-10) and Cyproterone Acetate were separately diluted in DMSO/2-hydroxypropyl β-cyclodextrin (vehicle).

The test was carried out comparing the anti-tumor activity of cortexolone 17α-valerate-21-propionate (CB-03-10) at two different dosages (approximately 8.6 mg/kg and 43 mg/kg) versus the vehicle (i.e. 0.4% (v/v) tween 80 and 0.5% (w/v) carboxymethylcellulose in normal saline) and versus the comparator Cyproterone Acetate at two different dosages (7.4 mg/kg and 37 mg/kg).

$1 \times 10^6$ MiaPaca-2 cells suspended in matrigel were subcutaneously injected into 6 week old athymic nude mice.

The treatment with the tested compound, with the vehicle and with the comparative compound was initiated after the tumor has reached a volume of 50 mm$^3$ after implantation, injecting subcutaneously 100 μL/mouse of low dose solution (approximately 230 μM) or 100 L/mouse of high dose solution (approximately 1150 μM) of cortexolone 17α-valerate-21-propionate (CB-03-10), vehicle and cyproterone acetate, respectively. Compounds and controls were administered subcutaneously daily for 28 days.

Tumors were measured every 4 days with a digital caliper.

Figure 2:
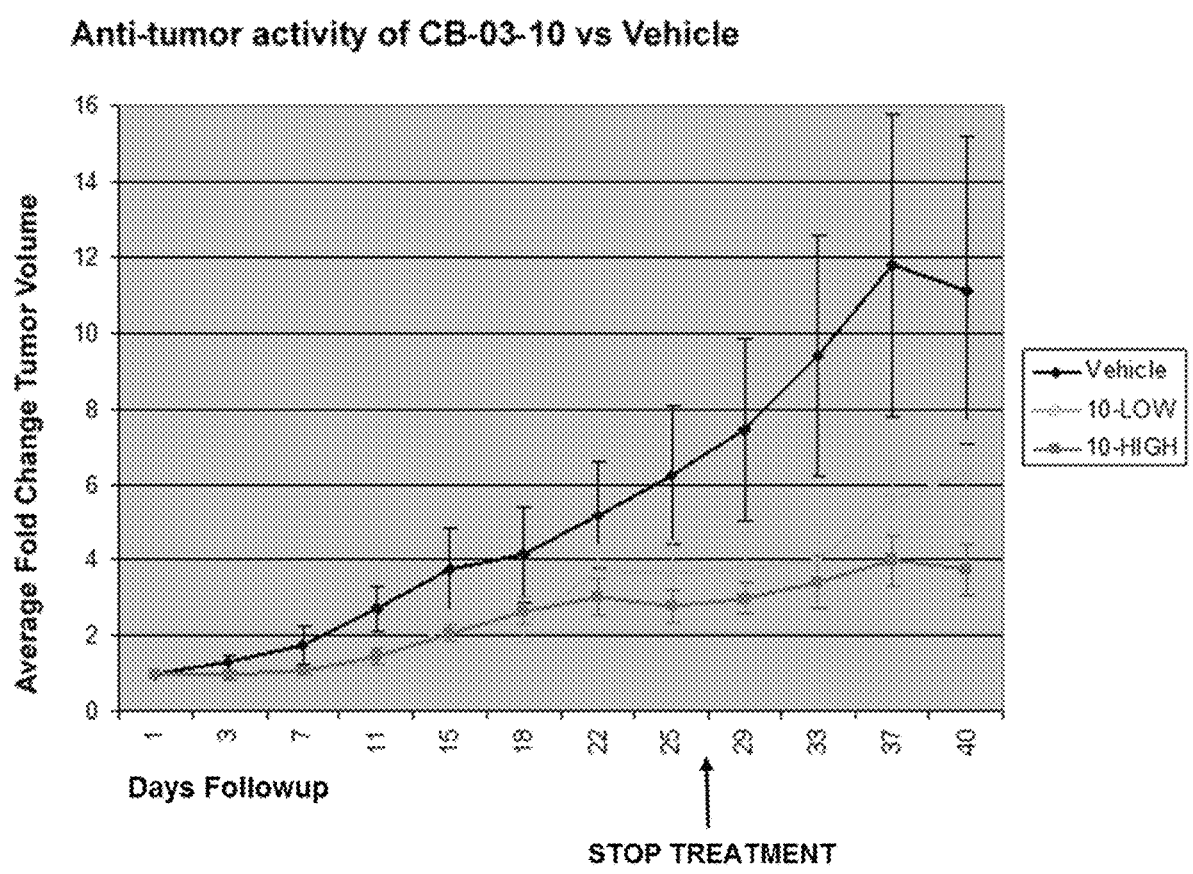
FIG. 2: Average fold change in pancreatic tumor volume, measured relatively to the start of SC treatment, in the xenograft animal model of nude mice (MiaPaca pancreatic cell line) with cortexolone 17α-valerate-21-propionate (in the figure referred to as "10" and as "CB-03-10") at low dose (230 μM) and at high dose (1150 μM). Reference to "Vehicle" is a control treated group with 0.4% (v/v) tween 80 and 0.5% (w/v) carboxymethylcellulose in normal saline. Mice were treated with the compound and vehicle SC daily for 28 consecutive days. The stop treatment arrow refers to the day when the treatment was ended.

The results are plotted in FIG. 2 as average change in tumor volume relative to the start of treatment. Tumor volume was calculated according to the formula $0.5236(r_1)^2(r_2)$ where $r_1 < r_2$.

Error bars are the SEM for 7 to 10 mice per treatment group. P values were calculated according to the Student's t test.

The high dose of Cortexolone 17α-valerate-21-propionate (CB-03-10) maintained the pancreatic tumor size increase to less than 5-fold the initial tumor size for the time of treatment. Moreover, when the treatment was stopped, the tumor size tended to increase again, but with a lower rate and extent. In contrast, the average tumor in the vehicle and in the Cyproterone Acetate treatment groups increased in size to 12-fold and more, bringing to the need of suppressing some of the animal of these groups for ethical reasons. From these data the antitumor activity of the compound of the present invention, cortexolone 17α-valerate-21-propionate (CB-03-10), is evident.

Figure 3:
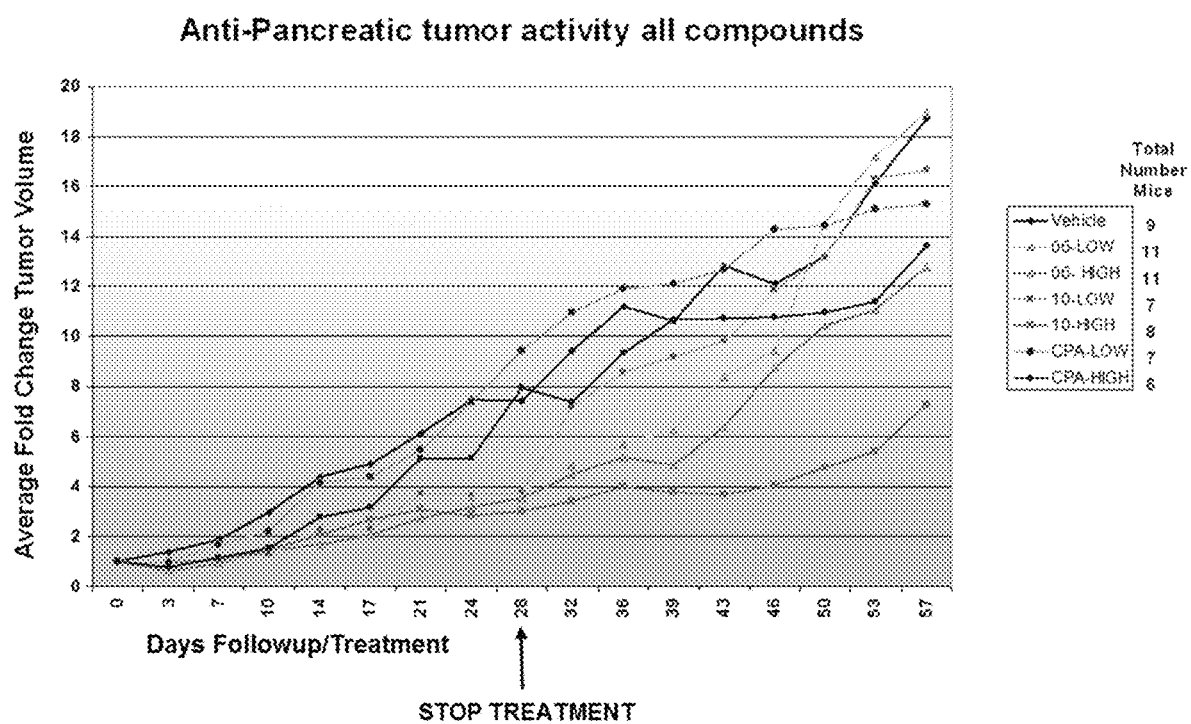
FIG. 3: Average fold change in pancreatic tumor volume relative to the start of SC treatment in the animal model of nude mice (MiaPaca pancreatic cell line) treated with Cyproterone Acetate (in the figure referred to as CPA), cortexolone 17α-valerate-21-propionate (in the figure referred to as "10") and cortexolone 17α-benzoate (in the figure referred to as "06") (each compound at low dose and at high dose) and with vehicle (i.e. 0.4% (v/v) tween 80 and 0.5% (w/v) carboxymethylcellulose in normal saline) treated control group. All mice were treated with the compound and vehicle SC daily for 28 consecutive days (days treatment). The stop treatment arrow refers to the day when the treatment was ended.
Figure 4:
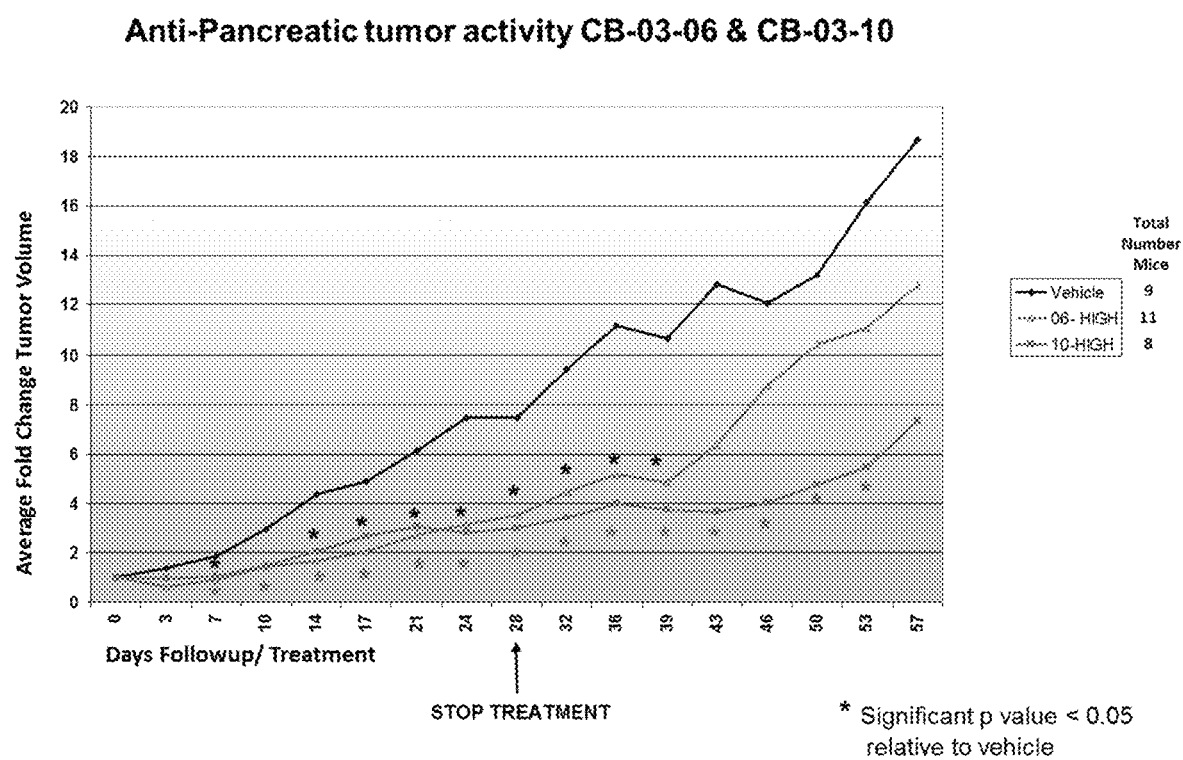
FIG. 4: Graph showing the P values Vs vehicle (i.e. 0.4% (v/v) tween 80 and 0.5% (w/v) carboxymethylcellulose in normal saline) treated control group of the best doses from FIG. 3. All mice were treated with the compound and vehicle SC daily for 28 consecutive days (days treatment). The stop treatment arrow refers to the day when the treatment was ended.

From the data of Examples 5 and 6, the in vivo antitumor activity of cortexolone 17α-benzoate and cortexolone 17α-valerate-21-propionate (CB-03-10) in vivo against the pancreatic tumor was confirmed, and both the compounds had an antitumor activity higher than Cyproterone Acetate in the same animal model (see FIG. 3).

Example 7: In-Vitro Therapeutic Index on Pancreatic Cancer Cells Lines

In order to evaluate the safety of the compounds to be tested in the cell lines viability experiments, all the factor impacting on the cell survival and viability should be taken into account. In this sense, the evaluation of intrinsic toxicity of compound and comparators is really important. The ratio from $IC_{50}$ of the compounds on peripheral blood mononuclear cells (PBMC) and the $IC_{50}$ on cancer cell lines constitute the Therapeutic Index and show what is the safer compound to be tested.

The $IC_{50}$ in PBMC were tested in 2 different activation status:
stimulated—actively dividing cells
resting—quiescent, non-dividing cells
Results are reported in the below tables, relevant to, respectively, stimulated PBMC and resting PBMC:

$IC_{50}$(microM) on Stimulated PBMC

Experiment 1

| Cell lines | CB-03-06 [Cortexolone 17α-benzoate] $IC_{50}$ (microM) | CB-03-10 [Cortexolone 17α-valerate-21-propionate] $IC_{50}$ (microM) | Cyproterone Acetate $IC_{50}$ (microM) | Enzalutamide $IC_{50}$ (microM) |
|---|---|---|---|---|
| Panc1 | 23 | 68 | 52 | 159 |
| MiaPaca2 | 17 | 34 | 39 | 79 |
| PBMC | 113 | 106 | 63 | 52 |

Experiment 2

| Cell lines | CB-03-06 [Cortexolone 17α-benzoate] $IC_{50}$ (microM) | CB-03-10 [Cortexolone 17α-valerate-21-propionate] $IC_{50}$ (microM) | Cyproterone Acetate $IC_{50}$ (microM) | Enzalutamide $IC_{50}$ (microM) |
|---|---|---|---|---|
| Panc1 | 28 | 60 | 46 | 110 |
| MiaPaca2 | 20 | 37 | 39 | 65 |
| PBMC | 97 | 94 | 62 | 90 |

In parallel the same experiments have been repeated on resting PBMC obtaining the results here below.

$IC_{50}$(microM) on Resting PBMC

Experiment 1

| Cell lines | CB-03-06 [Cortexolone 17α-benzoate] $IC_{50}$ (microM) | CB-03-10 [Cortexolone 17α-valerate-21-propionate] $IC_{50}$ (microM) | Cyproterone Acetate $IC_{50}$ (microM) |
|---|---|---|---|
| Panc1 | 23 | 68 | 52 |
| MiaPaca2 | 17 | 34 | 39 |
| PBMC | 100 | 114 | 18 |

| Cell lines | CB-03-06 [Cortexolone 17α-benzoate] $IC_{50}$ (microM) | CB-03-10 [Cortexolone 17α-valerate-21-propionate] $IC_{50}$ (microM) | Cyproterone Acetate $IC_{50}$ (microM) |
|---|---|---|---|
| Panc1 | 28 | 60 | 46 |
| MiaPaca2 | 20 | 37 | 39 |
| PBMC | 85 | 120 | 84 |

The resulting Therapeutic Index (TI) calculated on stimulated PBMC is reported in the tables below:

Experiment 1

| Cell lines | CB-03-06 TI [Cortexolone 17α-benzoate] | CB-03-10 TI [Cortexolone 17α-valerate-21-propionate | Cyproterone Acetate TI | Enzalutamide TI |
|---|---|---|---|---|
| Panc1 | 5 | 2 | 1 | 0 |
| MiaPaca2 | 7 | 3 | 2 | 1 |

| Cell lines | CB-03-06 TI [Cortexolone 17α-benzoate] | CB-03-10 TI [Cortexolone 17α-valerate-21-propionate | Cyproterone Acetate TI | Enzalutamide TI |
|---|---|---|---|---|
| Panc1 | 3 | 2 | 1 | 1 |
| MiaPaca2 | 5 | 3 | 2 | 1 | and the resulting Therapeutic Index calculated on resting PBMC is reported in the tables below:

TI on resting PBMC

Experiment 1

| Cell lines | CB-03-06 TI [Cortexolone 17α-benzoate] | CB-03-10 TI [Cortexolone 17α-valerate-21-propionate | Cyproterone Acetate TI |
|---|---|---|---|
| Panc1 | 4 | 2 | 0 |
| MiaPaca2 | 6 | 3 | 0 |

Experiment 2

| Cell lines | CB-03-06 TI [Cortexolone 17α-benzoate] | CB-03-10 TI [Cortexolone 17α-valerate-21-propionate | Cyproterone Acetate TI |
|---|---|---|---|
| Panc1 | 3 | 2 | 4 |
| MiaPaca2 | 4 | 3 | 1 |

In the tables, the 0 value indicates higher toxicity in PBMC than in the cancer cell lines

Example 8: In-Vitro Antitumor Activity of Cortexolone 17α-Benzoate and Cortexolone 17α-Valerate-21-Propionate (CB-03-10) on Epithelial Intestinal Cancer Cell Lines The experiment was performed to test and define anticancer activity in vitro of Cortexolone 17α-benzoate and cortexolone 17α-valerate-21-propionate on cell lines representatives of epithelial intestinal tumors, namely HT29. The experiment method consisted in:

1. Monolayer HT-29 cells were plated in: 96-wells plates at the density of $2\times10^4$ cells/mL. The cells plated were kept at 37° C. in 5% $CO_2$ and left to attach for 24 h.
2. Thereafter the cells were incubated for 72 h with the test compounds at the concentrations each of 0.16, 0.8, 4, 20, 100 and 500 mM.
3. After 72 h of treatment, the MTT colorimetric assay was performed.

The aim of the test was to determine the concentration at which each compound kills 50% of the cancer cells ($IC_{50}$) in view of a potential application of the compound in in vivo animal test.

Data were analyzed using nonlinear regression least squares curve fit in Prizm statistical analysis software.

The $IC_{50}$ value found for each line is reported in the following table.

Inhibition (%) at different micromolar concentration for the two products on HT29

| Micromolar concentrations | CB-03-10 [Cortexolone 17α-valerate-21-propionate] | CB-03-06 [Cortexolone 17α-benzoate] |
|---|---|---|
| 0.8 | 0.44% | −1.55% |
| 4 | 14.23% | 20.40% |
| 20 | 25.49% | 53.60% |
| 100 | 89.77% | 92.24% |
| 500 | 92.10% | 92.31% |

The $IC_{50}$ values calculated for the two product (reported here below) show that both compounds show an evident anticancer activity on the HT29.

$IC_{50}$ Calculated (Micromolar Concentration)

| | |
|---|---|
| CB-03-06 | 15.97 |
| CB-03-10 | 34.16 |

Example 9: In-Vitro Therapeutic Index on Epithelial Intestinal Cancer Cells Lines In order to evaluate the safety of the compounds to be tested in the cell lines viability experiments, all the factor impacting on the cell survival and viability should be taken into account. In this sense, the evaluation of intrinsic toxicity of compound and comparators is really important. The ratio between $IC_{50}$ of the compounds on PBMC and the $IC_{50}$ on cancer cell lines constitute the Therapeutic Index, a parameter important to define the product efficacy in safe conditions.

The $IC_{50}$ in PBMCs were tested in 2 different activation status:

Stimulated—actively dividing cells

Resting—quiescent, non-dividing cells.

The resulting Therapeutic Index (TI) calculated on Stimulated and Resting PBMC are reported in the hereunder tables:

Experiment 1

| Product | CB-03-06 (TI)[Cortexolone 17α-benzoate] | CB-03-10 (TI)[Cortexolone 17α-valerate-21-propionate |
|---|---|---|
| Stimulated | 7 | 3 |
| Resting | 6 | 3 |

Experiment 2

| Product | CB-03-06 (TI)[Cortexolone 17α-benzoate] | CB-03-10 (TI)[Cortexolone 17α-valerate-21-propionate |
|---|---|---|
| Stimulated | 6 | 3 |
| Resting | 5 | 4 |

From these data the anti-tumoral activity and safety of the compound of the present invention, cortexolone 17α-valerate-21-propionate, was confirmed versus the epithelial intestinal cancer cells.

Example 10—Synthesis of Cortexolone 17α-Benzoate

Cortexolone 17α-benzoate was prepared according to a synthesis scheme including the following steps:

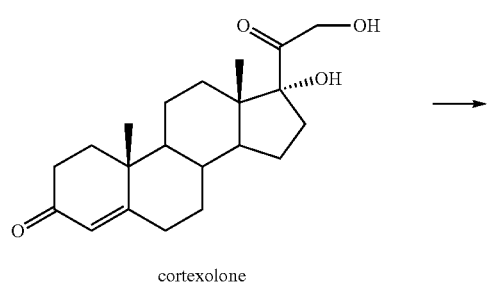

cortexolone

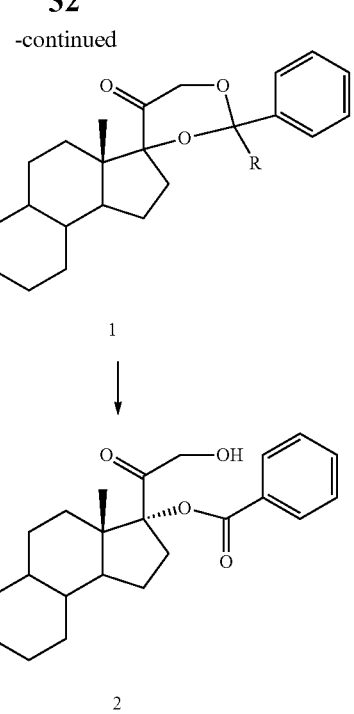

1

2

R = methyl, ethyl

In Step 1 Cortexolone was dissolved in a suitable solvent (e.g. ethyl acetate). Pyridinium tosilate or p-toluene sulfonic acid was added in catalytic amount (1-10% mol) followed by tri-alkyl orthobenzoate (R=methyl or R=ethyl). The reaction mixture was heated up to 80° C. for 3 to 6 hours.

After removal of the solvent and crystallization in alcoholic solvent, cortexolone orthobenzoate 1 was obtained as a solid.

In Step 2, cortexolone orthobenzoate 1 (R=methyl or R=ethyl) was dissolved in an alcoholic solvent (e.g. methanol) and treated with 0.1N acetic buffer at reflux. After removal of the solvent, the residue was purified by treatment with demi water and cortexolone-17-α-benzoate was recovered as a solid.

Example 11—Synthesis of Cortexolone 17α-Valerate-21-Propionate (CB-03-10) (3) and Cortexolone 17α-Valerate (CB-03-05) (2)

Cortexolone 17α-valerate-21-propionate (CB-03-10) was prepared according to the following synthetic scheme:

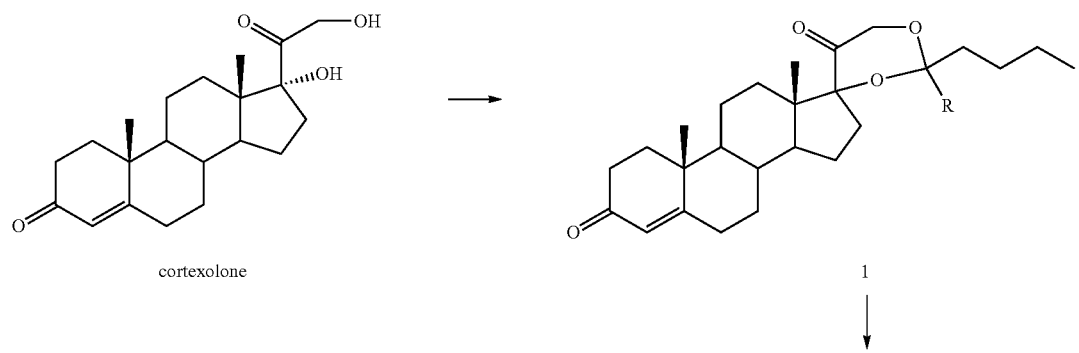

1

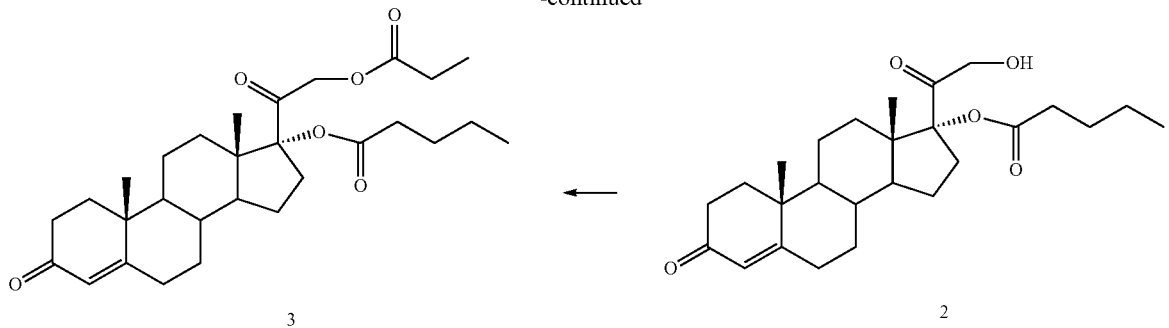

3
R = methyl, ethyl

2

Step 1: Cortexolone was dissolved in a suitable solvent (e.g. ethyl acetate). Pyridinium tosilate or p-toluene sulfonic acid was added in catalytic amount (1-10% mol), followed by tri-alkyl orthovalerate (R=methyl or R=ethyl). The reaction mixture was heated up to 80° C. for 3-5 hours and, after removal of the solvent and crystallization in alcoholic solvent, cortexolone orthovalerate 1 was obtained.

In Step 2, cortexolone orthovalerate 1 (R=methyl or R=ethyl) was dissolved in an alcoholic solvent (e.g. methanol) and treated with 0.1N acetic buffer (pH 3 to 3.9) at reflux. After the removal of the solvent followed by treatment with purified water, cortexolone-17α-valerate 2 was recovered as a solid.

In Step 3, cortexolone-17α-valerate 2 was dissolved in pyridine and added with 1 equivalent of propionyl chloride. When the conversion was complete, the mixture was diluted with water, and the product 3 was recovered as a solid and purified by crystallization with alcohols.

Example 12—Analysis of In Vitro Anti-Cancer Activity of Cortexolone Derived Compound CB-03-10

The capability of CB-03-10 to inhibit the growth of cancer cell lines established in vitro was tested.

Figure 5:
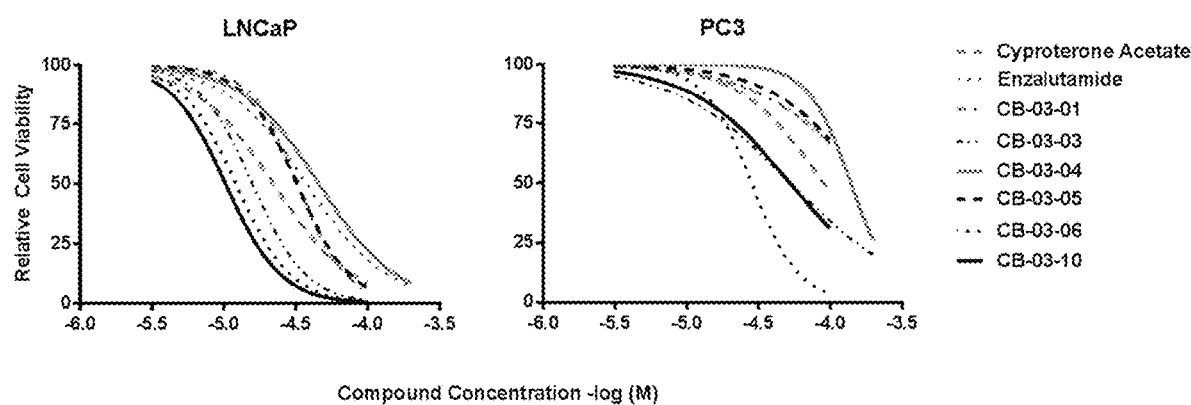
FIGS. 5A and 5B: Dose Titration of cytotoxicity of cortexolone-derived compounds in human prostate (A) and pancreatic (B) cancer cell lines.
Figure 5:
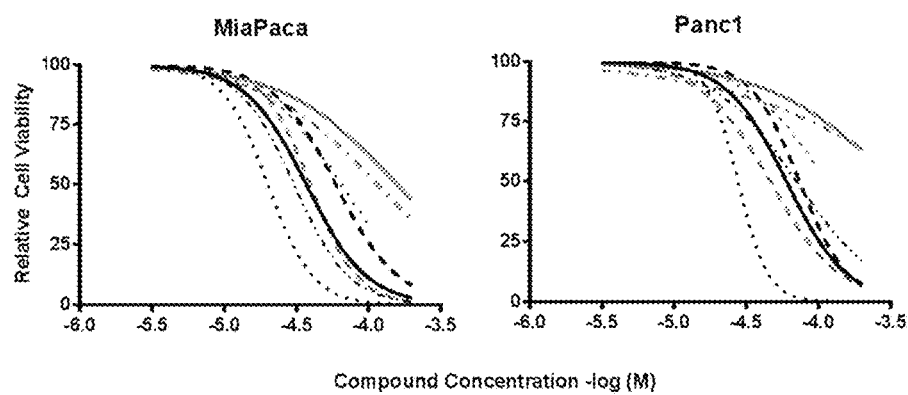

Cancer cell lines were seeded at 3000 cells in 96-well flat bottom plates in complete media containing 2% charcoal stripped bovine serum. After 24 hours the test compounds or DMSO/vehicle (0.1% final concentration as negative control) were added. CPA and Enzalutamide, two potent recognized anti-androgens were used as positive control for cell cytotoxicity. After 3 days, viable cell numbers were quantitated using an ATP-dependent cell viability assay (Promega Cell Titer Glo). In FIG. 5 is shown a dose titration of the cytotoxicity activity of cortexolone derived compounds on human and pancreatic cell lines.

The determination of the concentration at which each compound kills 50% of the cancer cells ($IC_{50}$) was performed to express the capability of CB-03-10 and other compounds to inhibit cancer cell growth. Each compound was titrated from 3 µM to 200 µM. After 3 days, viable cell numbers were quantitated using an ATP-dependent proliferation assay. Data shown in Table I were analyzed using nonlinear regression least squares curve fit in Prizm statistical software.

TABLE I $IC_{50}$ of CB-03-10 tested in vitro in Prostate & Pancreatic Cancer Cell Lines

| Tissue Type | Cell Line Name | CB-03-01 C17 prop | CB-03-03 C17, 21 but | CB-03-04 9dehy 17 but | CB-03-05 C17 val | CB-03-06 C17 ben | CB-03-10 C17, 21 val | Enzalutamide | CPA |
|---|---|---|---|---|---|---|---|---|---|
| Prostate Cancer | LNCaP | 33 | 16 | 46 | 32 | 12 | 10 | 38 | 22 |
| | PC3 | 190 | 53 | 140 | 170 | 28 | 53 | 180 | 90 |
| Pancreatic Cancer | Panc1 | 490 | 70 | 340 | 74 | 28 | 60 | 110 | 46 |
| | MiaPaca2 | 110 | 30 | 160 | 59 | 20 | 37 | 65 | 39 |

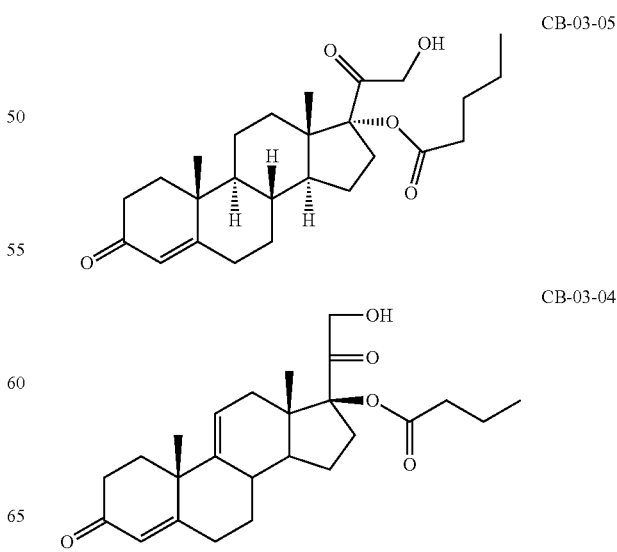

CB-03-05

CB-03-04

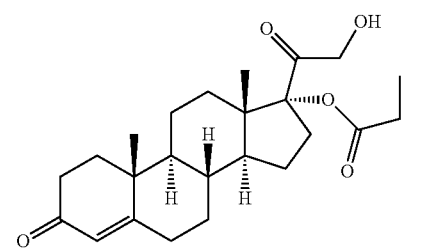

CB-03-01

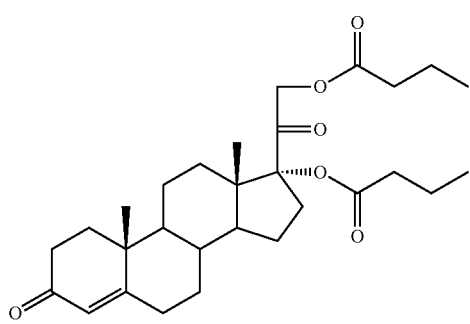

CB-03-03

It is clear from the data shown in FIG. 5 and Table I that cortexolone derived compounds kills cancer cells at various concentration and IC$_{50}$. CB-03-10 kills prostate cancer cells (panel a) better than potent anti-androgen CPA. More importantly CB-03-10 inhibited in vitro growth of prostate cancer cell better then Enzalutamide a novel and potent anti-androgen drug used currently in clinic as first choice for androgen dependent prostate cancers.

Interestingly, CB-03-10 inhibits growth of fast growth pancreatic cell lines (panel b) that are known to express Androgen Receptor (AR) a very low levels. These data suggest an independent mechanism of action related to cytotoxicity then the anti-androgen activity.

Example 13—Analysis of Androgen Receptor Expression on Tested Cancer Cell Lines

A FACS assay was performed on prostate and pancreatic cell lines tested in Table I to better understand the relationship between AR expression on cancer cells lines and the capability of CB-03-10 to inhibit cancer cell growth.

Figure 6:
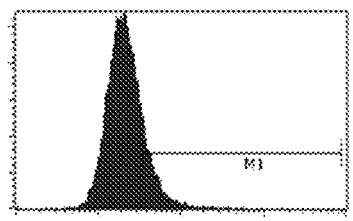
FIGS. 6A-6D: Androgen Receptor Expression levels on cancer cell lines: (A) PC-3 prostate; (B) LNCaP prostate; (C): MiaPaca-2 pancreatic; and (D): Panc-1 pancreatic.
Figure 6:
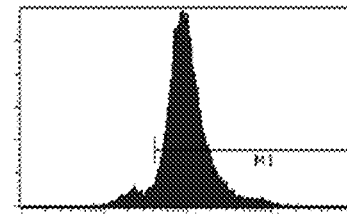
Figure 6:
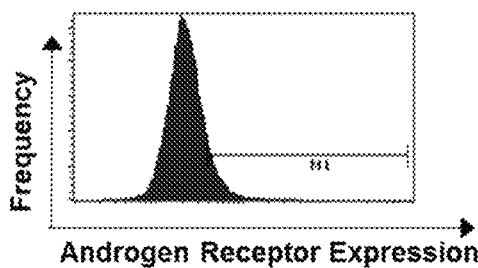
Figure 6:
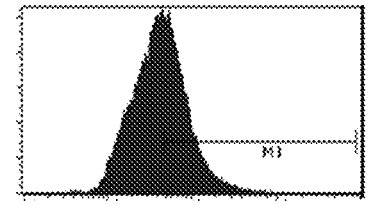

FIG. 6 shows the level of AR expression on the tested cancer cells. As expected, FACS analysis AR expression in prostate and pancreatic cell lines are consistent with published expression levels: LNCaP>Panc1>PC3=MiaPaca2.

To better clarify the correlation between AR and IC$_{50}$ Table I was implemented adding the AR expression of the tested cancer cell lines (Table II).

TABLE II

AR expression of Prostate & Pancreatic Cancer Cell Lines and IC$_{50}$ of Cortexolone-derived Compounds

| Cell Line Name | CB-03-01 C17 prop | CB-03-03 C17, 21 but | CB-03-04 9dehy 17 but | CB-03-05 C17 val | CB-03-06 C17 ben | CB-03-10 C17, 21 val | Enza-lutamide | CPA | AR Expression |
|---|---|---|---|---|---|---|---|---|---|
| LNCaP | 33 | 16 | 46 | 32 | 12 | 10 | 38 | 22 | 9 |
| PC3 | 190 | 53 | 140 | 170 | 28 | 53 | 180 | 90 | 1 |
| Panc1 | 490 | 70 | 340 | 74 | 28 | 60 | 110 | 46 | 4 |
| MiaPaca2 | 110 | 30 | 160 | 59 | 20 | 37 | 65 | 39 | 1 |

As expected the growth inhibition shown by potent anti-androgens CPA and Enzalutamide correlates with AR expression in prostate cancer cells. The inhibitory activities of CB-03-10, also correlate (less strictly) with AR expression in prostate cancer cells. However, there is an inverse correlation between AR expression and inhibitory activities in the pancreatic cancer cells. All tested compounds were more active in the lower AR expressing MiaPaca2 (AR+/−) compared to the Panc1 cells (AR+). This result hints on a possible AR-independent mechanism of action in pancreatic cancer. CB-03-10 is one of the most potent compounds in the series. Notably, CB-03-10 is more potent than Enzalutamide in prostate cancer cell lines.

Example 14—Analysis of In Vitro Anti-Cancer Activity of Cortexolone Derived Compounds, in Particular CB-03-10, on a Larger Sample of Cancer Cell Lines Derived from Solid Tumors Since the cytotoxic activity of CB-03-10 seemed to not correlate with AR expression, a larger sample of solid tumors was tested. MCF7, a breast cancer cell line (AR$^{+/-}$), an additional pancreatic cell line with higher AR expression (BxPC3) and intestinal cancer cell line (HT29) (AR$^-$) were added to the previous panel. Results are depicted in Table III.

TABLE III

IC$_{50}$ of CB-03-10 on cancer cell lines characterized by AR and GR expression

| | | in vitro proliferation IC50 (µM) | | | Genotype | |
|---|---|---|---|---|---|---|
| | | | | | AR protein | GR protein |
| Tissue Type | Cell Line Name | CB-03-05 C17 val | CB-03-10 C17, 21 val | Enza-lutamide | expression relative to PC3 | expression relative to LNCaP |
| Prostate Cancer | LNCaP | 32 | 10 | 38 | 9 | 1 |
| | PC3 | 170 | 53 | 180 | 1 | 2 |
| | 22Rv1 | | 18 | | positive based on literature | negative based on literature |
| Pancreatic Cancer | Panc1 | 74 | 60 | 110 | 4 | positive based on literature |
| | MiaPaca2 | 59 | 37 | 65 | 1 | 4 |
| | BxPC3 | | 30 | 127 | 3 | positive based on literature |
| Breast Cancer | MCF7 | 50 | 28 | 129 | 1 | 2 |
| | MDA-MB-231 | not active | 106 | 200 | 1 | 5 |
| Colon Cancer | HT29 | 530 | 14 | 150 | 1 | 2 |
| Healthy Lymphocyte | PBMC RESTING | 120 | 120 | | nd | positive based on literature |
| | PBMC STIMULATED | 130 | 94 | 90 | nd | positive based on literature |

CB-03-10 strongly inhibits cell viability of multiple cancer cell lines from different epithelial origin. The compound's cytotoxicity activity does not correlate with expression of AR. Additionally, CB-03-10 is more potent than Enzalutamide in all cancer cell lines tested.

Example 15—Therapeutic Index of Cortexolone Derived Compounds on Different Cancer Cell Lines The therapeutic index (TI) (also referred to as therapeutic window or safety window or sometimes as therapeutic ratio) is a comparison of the amount of a therapeutic agent that causes the therapeutic effect to the amount that causes toxicity. IC$_{50}$ of the compounds was determined on fresh cells isolated from human blood (PBMC). The compounds toxicity was determined as follow:

Therapeutic Index=Safety/Potency=IC$_{50}$ stimulated PBMC/IC$_{50}$ cancer cell The results are shown in Table IV

TABLE IV

Therapeutic index of cortexolone derived compounds on a panel of cancer cell lines.

| Tissue Type | Cell Line Name | CB-03-01 C17 prop | CB-03-03 C17, 21 but | CB-03-04 9dehy 17 but | CB-03-05 C17 val | CB-03-06 C17 ben | CB-03-10 C17, 21 val | Enza lutamide | CPA |
|---|---|---|---|---|---|---|---|---|---|
| In vitro proliferation IC50 (micro Molar) | | | | | | | | | |
| Prostate Cancer | LNCaP | 33 | 16 | 46 | 32 | 12 | 10 | 38 | 22 |
| | PC3 | 190 | 53 | 140 | 170 | 28 | 53 | 180 | 90 |
| Pancreatic Cancer | Panc1 | 490 | 70 | 340 | 74 | 28 | 60 | 110 | 46 |
| | MiaPaca2 | 110 | 30 | 160 | 59 | 20 | 37 | 65 | 39 |
| | BxPC3 | | | | | 28 | 30 | 127 | |
| Breast Cancer | MCF7 | 121 | 32 | 88 | 50 | 25 | 28 | 129 | 64 |
| Colon Cancer | HT29 | | | 51 | 30 | 10 | 14 | 150 | |
| Healthy Lymphocyte | PBMC STIMULATED | 0.1 | 140 | 360 | 130 | 97 | 94 | 90 | 62 |
| Therapeutic Index = IC50 resting PBMC/IC50 cancer cell | | | | | | | | | |
| Prostate Cancer | LNCaP | 0 | 9 | 8 | 4 | 8 | 9 | 2 | 3 |
| | PC3 | 0 | 3 | 3 | 1 | 3 | 2 | 1 | 1 |
| Pancreatic Cancer | Panc1 | 0 | 2 | 1 | 2 | 3 | 2 | 1 | 1 |
| | MiaPaca2 | 0 | 5 | 2 | 2 | 5 | 3 | 1 | 2 |
| | BxPC3 | | | | | 3 | 3 | 1 | |
| Breast Cancer | MCF7 | 0 | 4 | 4 | 3 | 4 | 3 | 1 | 1 |
| Colon Cancer | HT29 | | | 7 | 4 | 6 | 3 | | |
| Healthy Lymphocyte | PBMC Stim | 1 | 1 | 1 | 1 | 1 | 1 | 1 | 1 |

All cortexolone derived compounds show a robust safety profile. CB-03-10 shows a high therapeutic index. This reveals that CB-03-10 has a safer profile compared to CPA and Enzalutamide.

Example 16—CB-03-10 Binding Affinity for the Androgen Receptor

The previous experiments demonstrated a strong cytotoxicity activity of CB-03-10 on cancer cell lines derived from tumors of different origins. This cytotoxic activity did not completely correlate with the anti-Androgen Receptor expression on the tested cancer cells. Based on this evidence assays to test the affinity of the compound to the AR were designed. To determine the relative binding affinities of CB-03-10 to the wild type AR a competition assay using Polar Screen kit from life Technologies was used. Briefly, the AR was added to a fluorescent androgen ligand (Fluormone™ AL Green) to from the complex AR-LBD. Competitors displaced the fluorescent Fluormone™ AL Green ligand from the AR-LBD causing the fluorescent ligand to tumble rapidly during its fluorescence lifetime, resulting in a low polarization value. Non competitors will not displace the fluorescent ligand from the complex, so the polarization value remains high. The shift in polarization value in the presence of test compounds is used to determine relative affinity of test compounds for AR-LBD.

CB03-10 affinity for AR receptor was 1.1E-06 ($IC_{50}$ molar); in the same assay the affinity of Dihydrotestosterone (a potent binder of AR receptor) was 1.1E-08.

CB-03-10 binding affinity for the AR receptor when compared to DHT is low and characterizes CB-03-10 as an AR potential binder

Example 17—CB-03-10 Transcriptional Activity on the Glucocorticoid Receptor

The androgen and glucocorticoid hormones elicit divergent and often opposing effects in cells, tissues, and animals. A wide range of physiological and molecular biological evidence suggests that the receptors that mediate these effects, the Androgen and Glucocorticoid Receptors (AR and GR, respectively), influence each other's transcriptional activity. CB-03-10 GR antagonist and agonist activities were tested in an in vitro assay. Briefly, human kidney epithelial cells were transfected with DNA construct containing GR binding sites linked to luminescent based reporter molecule. After 24 hours, cells were treated under antagonist or agonist modes. After an additional 24 hours, luminescence which is proportional to GR agonist transcriptional activity was quantitated.

Antagonist Assay was based on inhibition of luminescence induced by Dexamethasone (Dex).

Figure 7:
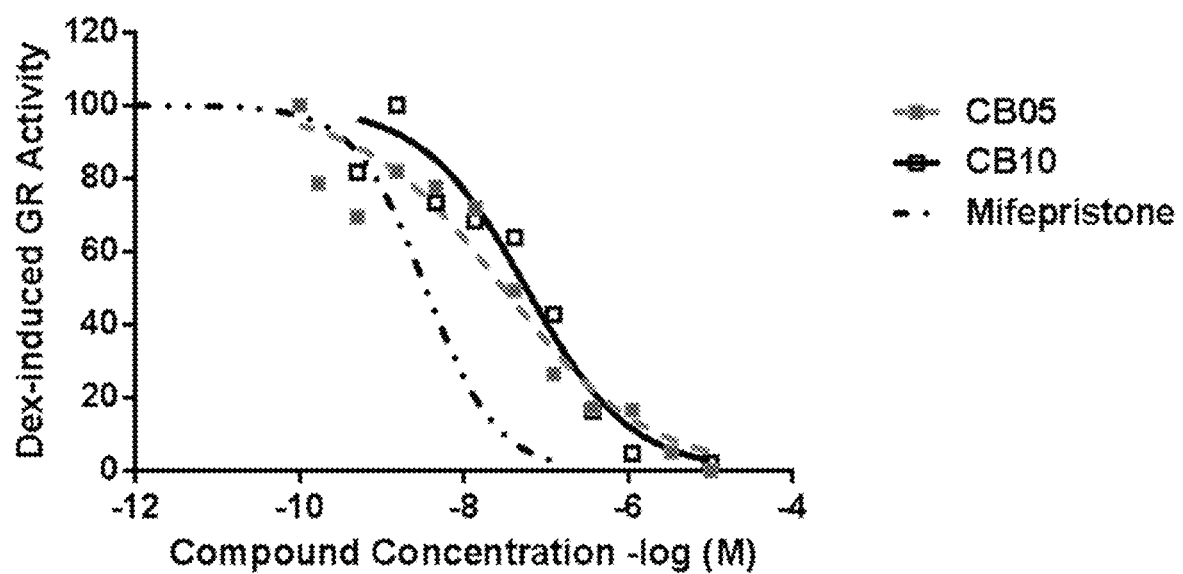
FIG. 7: CB-03-10 and CB-03-05 glucocorticoid_antagonist activity. Mifepristone is used as positive control (potent glucocorticoid antagonist)

The antagonist activity of CB-03-10 was compared to a known GR antagonist, Mifepristone (also called RU486) as shown in FIG. 7.

Agonist Assay—was based on induction of luminescence by CB-03-10

Figure 8:
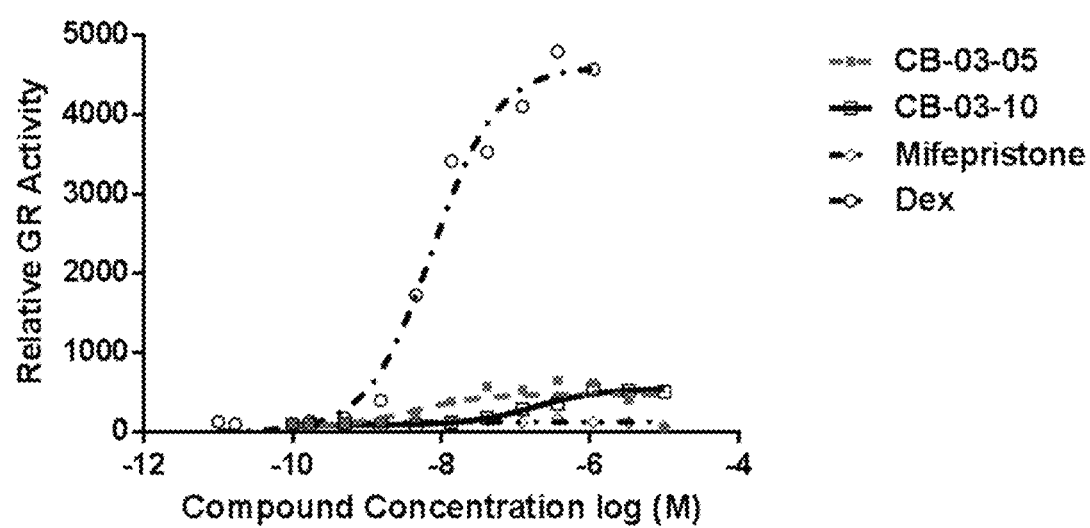
FIG. 8: CB-03-10 and CB-03-05 glucocorticoid agonist activity, Dexametasone (Dex) is used as positive control (potent glucocorticoid agonist)

The agonist activity of CB-03-10 was compared to a RU486 which is known to not have agonist activity. As shown in FIG. 8.

As shown in FIG. 7, CB-03-10 is a potent antagonist (10 times less than RU486). By contrast, CB-03-10 is essentially ineffective as GR agonist since very high concentrations are required to induce an activity that is 20% that of 50 nM Dex.

Example 18—CB-03-10 Induction of Apoptosis and Cell Cycle Arrest

Most of the cytotoxic anticancer drugs in current use have been shown to induce apoptosis in susceptible cells. The fact that disparate agents, which interact with different targets, induce cell death with some common features suggests that cytotoxicity is determined by the ability of the cell to engage this so-called 'programmed' cell death. CB-03-10 was evaluated to determine if the mechanism of cytotoxicity on cancer cell lines was mediated by apoptosis and cell cycle arrest. Cancer cell lines were seeded in 6-well flat bottom plates. After 24 hours test compounds or DMSO vehicle (negative control) were added. After an additional 24 hours cells were scraped and stained with fluorescein conjugated Annexin V and propidium iodide and analyzed by flow cytometry.

Figure 9:
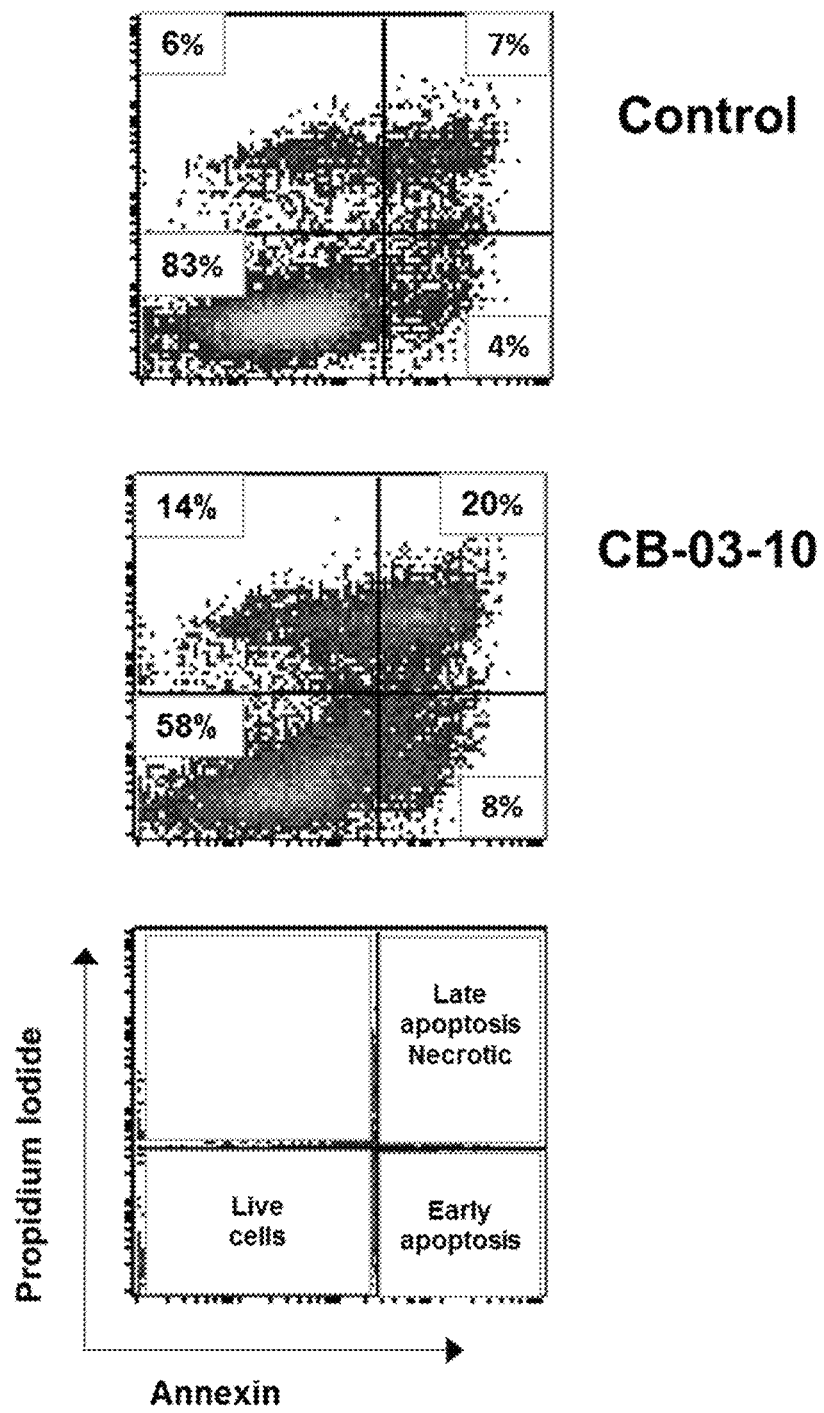
FIG. 9: CB-03-10 induction of apoptosis in MiaPaca2 cells.

FIG. 9 shows clearly how CB-03-10 is able to induce apoptosis in a pancreatic cancer cell lines. CB-03-10 induces apoptosis in a total of 28% cells (early and late apoptosis) vs only 11% by the control.

Figure 10:
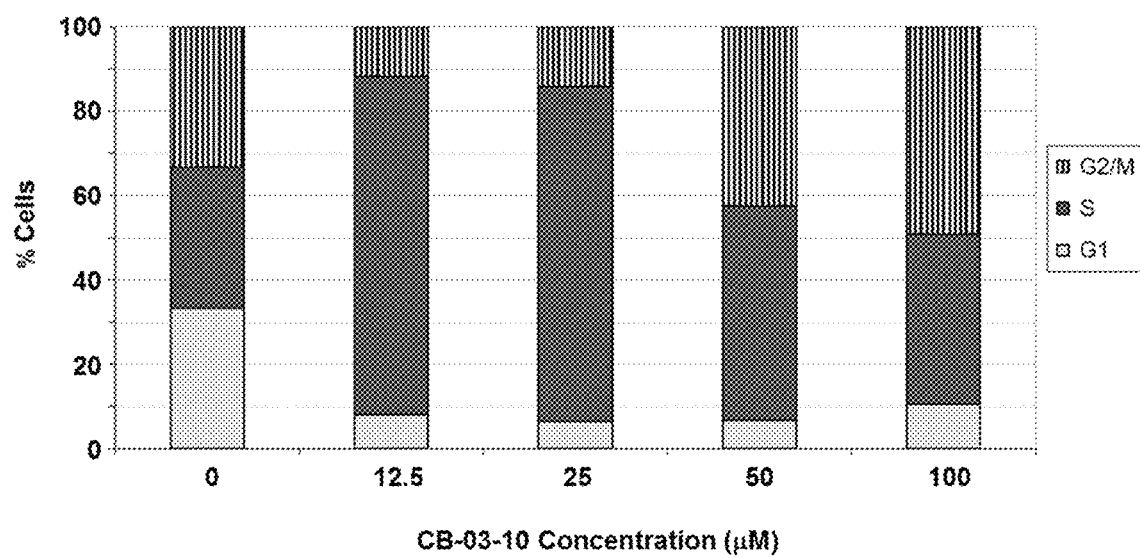
FIG. 10: Induction of cell cycle arrest by different concentrations of CB-03-10 in MiaPaca2 cells.

Apoptosis can occur at the G1/S or G2/M transition of the cell cycle. Cells were treated with CB-03-10 for 24 hours then fixed with paraformaldehyde and stained with propidium iodide. Data in FIG. 10 indicates CB-03-10 induces an S phase block at lower concentrations then a G2/M block at higher concentration. The lack of G1 block indicates no effect on p53. The S & G2/M blocks may indicate activity on cell cycle check point molecules. For S phase, a possible target is the cyclin dependent kinase 2 (CDK2). Gemzar and cisplatin are example drugs that act in S phase. For G2, a possible target is CDK1.

Example 19—Analysis of Caspase Induction by CB-03-10

From previous studies was determined that CB-03-10 induces apoptosis using Annexin V staining in MiaPaca2 cells. To better analyze the phenomenon the enzymatic activity of Caspase 8 (initiator caspase for Extrinsic Pathway) and Caspase 9 (initiator caspase for Intrinsic Pathway) and of Caspases 3 and 7 (effector caspases) were measured.

Figure 11:
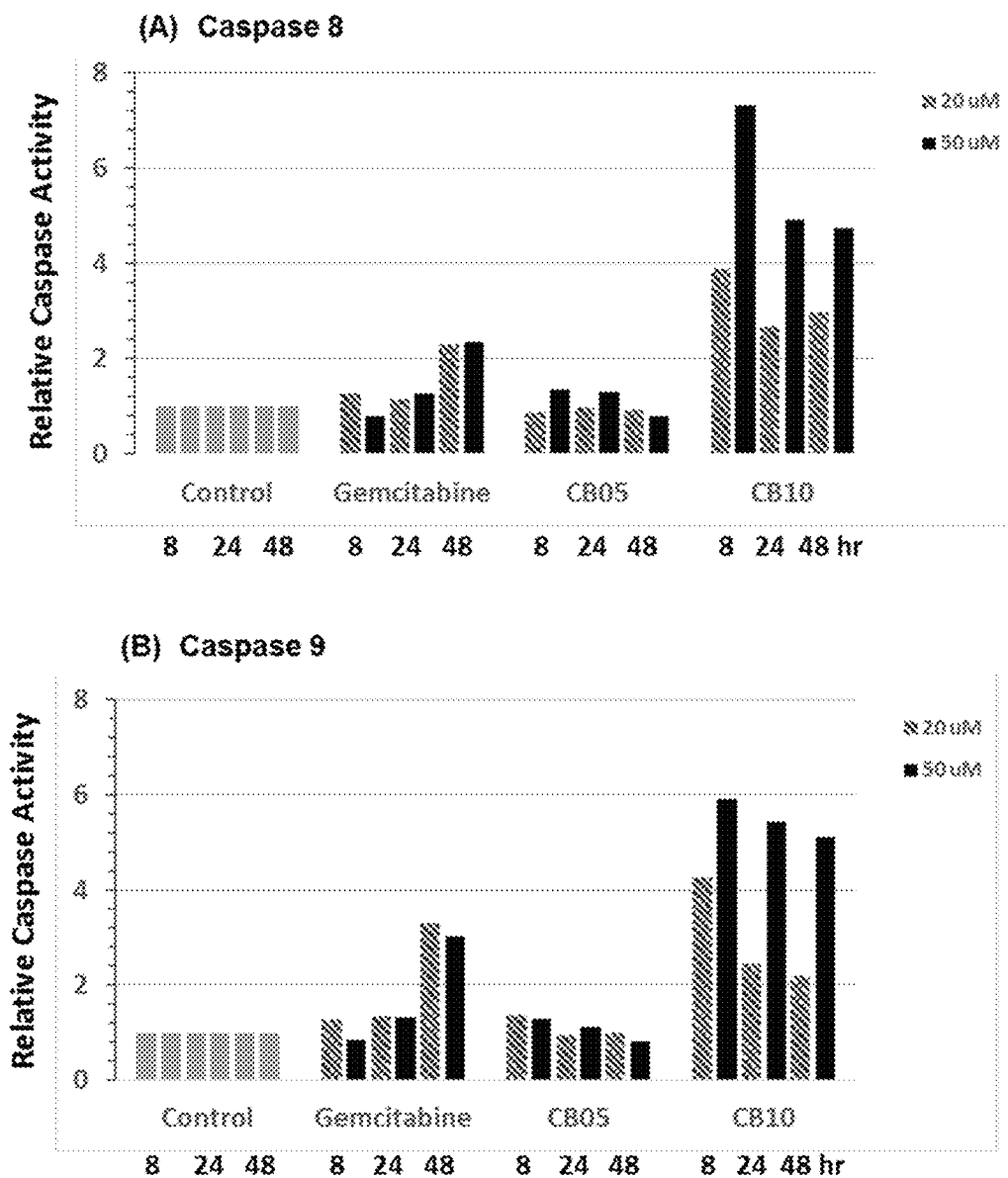
FIGS. 11A-11C; Time course of caspases activation in MiaPaca2 Cells (8-24-48 hours). 20 μM (striped bars) or 50 μM (solid bars) indicate the compound's concentrations. Gemcitabine is a potent anti pancreatic cytotoxic drug used and positive control. Caspases: (A): caspase 8; (B): caspase 9; and (C): caspase 3/4.
Figure 11:
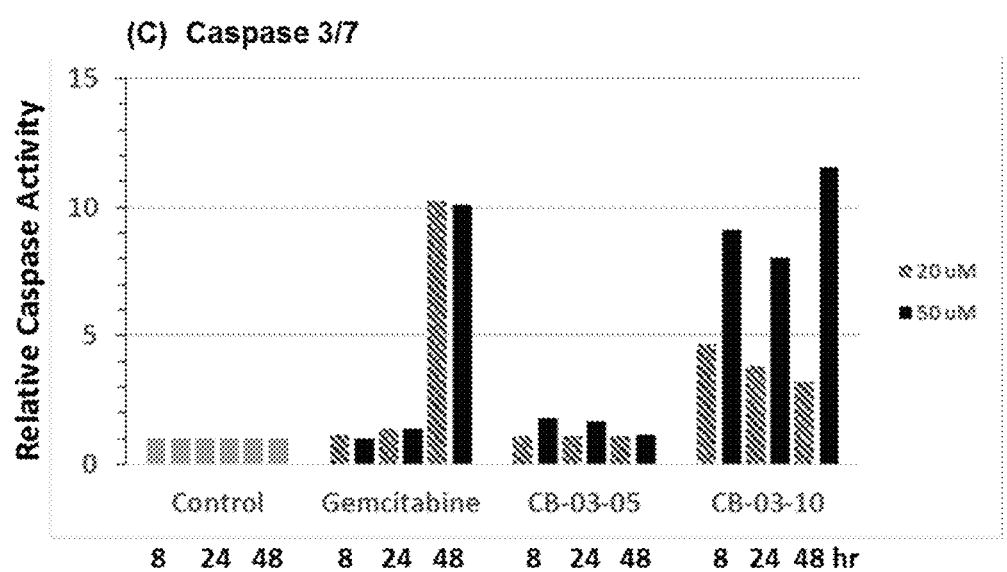

For this purpose, MiaPaca2 cells were seeded in 96 well flat bottom culture plates. After 24 hours test compounds were added to cells, Gemcitabine (a known pancreatic cancer chemotherapeutic agent) and DMSO were used as positive and negative control, respectively. After 8, 24, & 48 hours incubation with test compounds, cells were lysed in buffer containing the caspase 3/7 or 8 or 9 substrate and a stable luciferase in proprietary buffers. The lysates were transferred to white opaque plates before measuring luminescence in a Tecan Safire instrument. Parallel plates treated identically, were used to determine viable cells. All caspase activities were corrected for the number of viable cells. Results are shown in FIG. 11.

The activities of caspases 8 and 9 (panels A and B) were induced by CB-03-10. This induction was quick, dose-related, and already evident after 8 hours and was as high as 7-fold increase compared to control.

Gemcitabine (a known chemotherapy agent used for pancreatic cancer treatment) also induced caspase 8 and 9 activities but with a delayed and less potent response compared to CB-03-10. The 2, 3-fold increase in Caspase 8 and 9 activity is not seen until the 48 hours mark.

Caspase 3/7 (panel C) were induced by CB-03-10 also in this case already at 8 hours at and a really high level after 48 hours incubation. Interestingly CB-03-05 does not show a good profile for caspase activation. Gemcitabine increase in Caspase 3/7 activity is not seen until the 48 hours mark.

Figure 12:
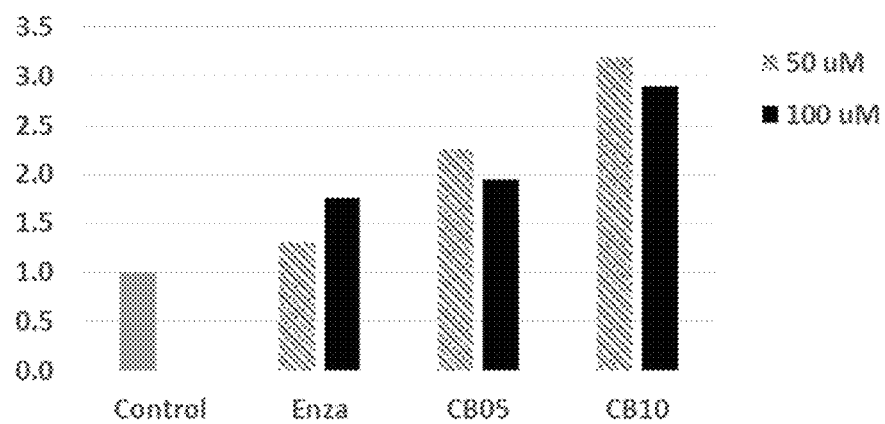
FIGS. 12A-12C: Caspase activation on LNCaP prostate cancer cell lines. Caspases: (A): caspase 8; (B): caspase 9; and (C): caspase 3/4.
Figure 12:
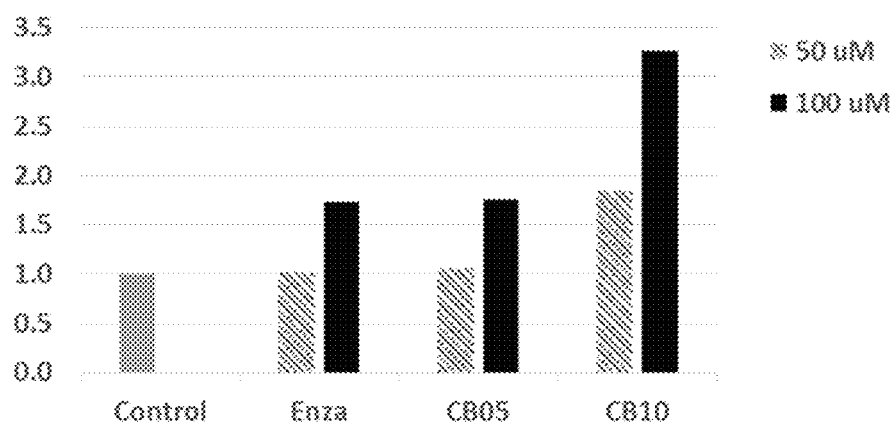
Figure 12:
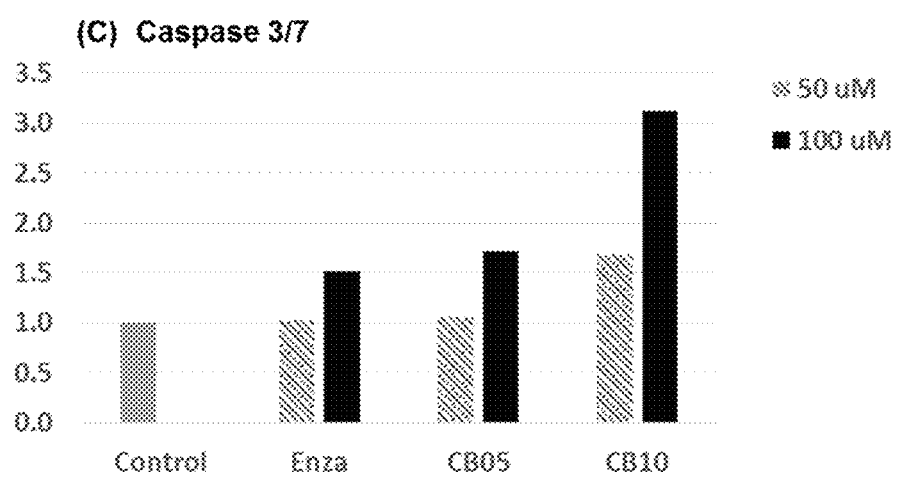

Same assay was repeated using LNCaP prostate cancer cell lines (FIG. 12). In this case the positive control is Enzalutamide, a potent and novel anti antiandrogen currently used in clinic to treat prostate cancer patients. The results are shown in FIG. 12 at 24 hours incubation when the caspase activities peaked.

The experiment clearly shows that CB-03-10 induced Initiator (8 and 9) and Effector (3/7) caspase activities better than Enzalutamide (used as positive control). These results showed CB-03-10 strong induction of caspases activity on prostate cancer cell lines, affecting both intrinsic and extrinsic pathways, confirming the inhibition observed on MiaPaca2 cell lines.

Example 20—CB-03-10 In Vitro Metabolism in Rat and Human Plasma

Figure 13:
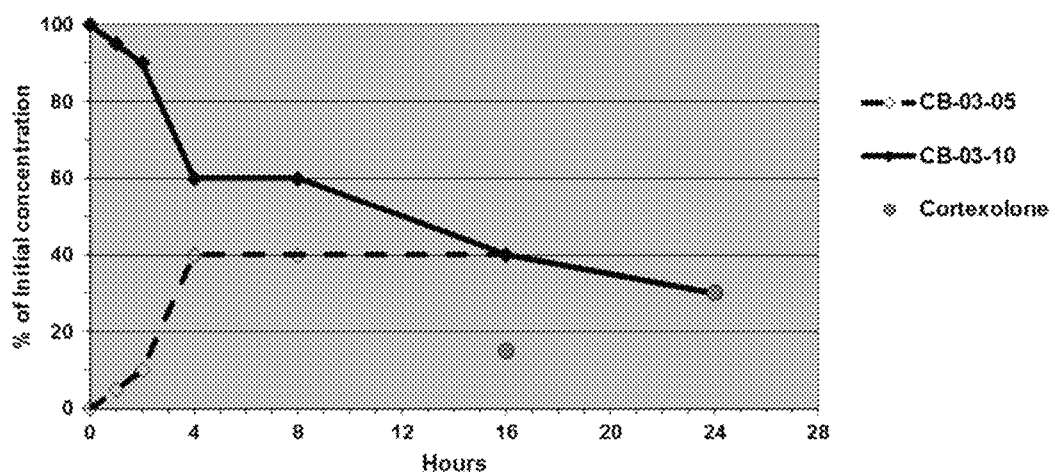
FIGS. 13A and 13B: In vitro metabolism of CB-03-10 and CB-03-05 in (A) Human and (B) Rat plasma.
Figure 13:
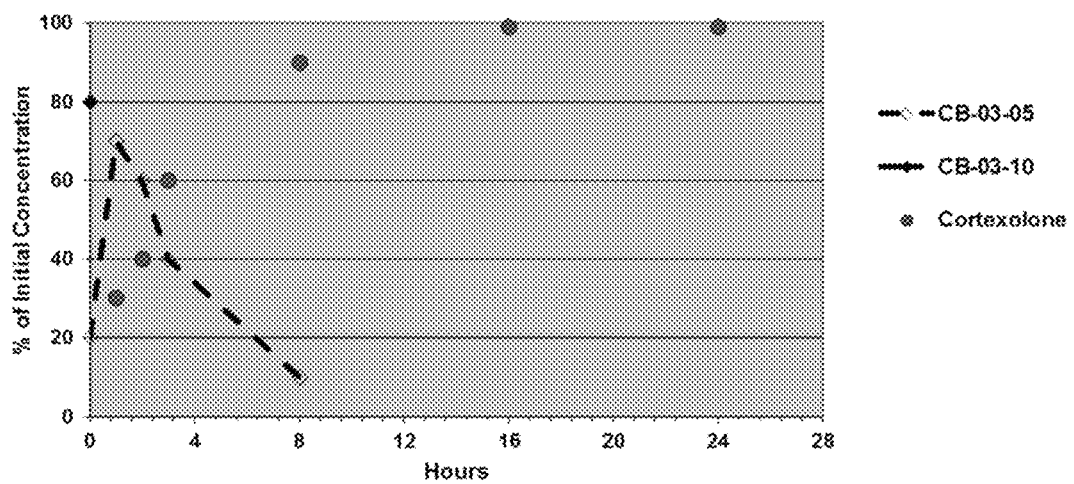

To obtain some insights on the metabolism of CB-03-10 in human and rat plasma, a specific assay was designed. Briefly the compound was incubated at different time in human and rat plasma at 37° C. After incubation the samples were tested for presence of the intact compound by liquid chromatography. The time course and concentration are shown in FIG. 13.

The results show that CB-03-10 is rapidly degraded to CB-03-05 in human plasma and it is degraded more rapidly in rat compared to human plasma.

Example 21—Analysis of CB-03-10 In Vivo Pharmacokinetic in an Animal Model (Mouse)

The pharmacokinetic of CB-03-10 was evaluated in plasma of mice after intravenous (IV), subcutaneous (SC) and oral administration (PO).

Mice (3 per group) were administered with the following doses, blood was collected at the indicated times. Plasma samples were analyzed by HPLC-MS/MS.

| Group | Dosing Route | Blood Collection Time Point |
|---|---|---|
| 1 | iv (20 mg/kg) | 10 min, 1 hr, 4 hr 30 min, 2 hr, 8 hr |
| 2 | SC (40 mg/kg) | 30 min, 2 hr, 8 hr 1 hr, 4 hr, 24 hr |
| 3 | PO (40 mg/kg) | 30 min, 2 hr, 8 hr 1 hr, 4 hr, 24 hr |

Figure 14:
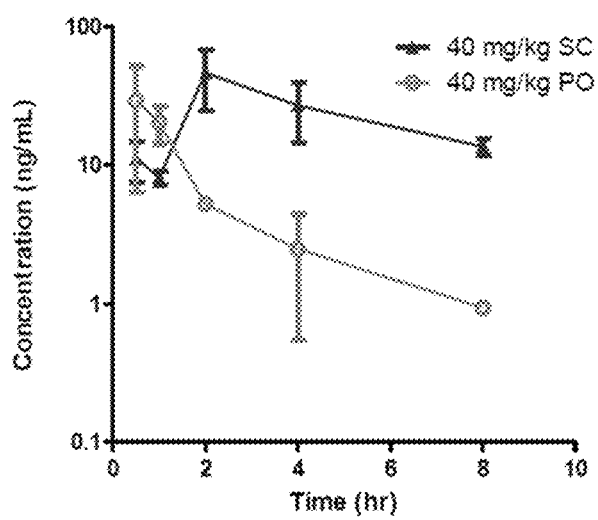
FIG. 14: CB-03-10 and CB-03-05 pharmacokinetics evaluated in vivo in plasma of mice after subcutaneous and oral administration.

CB-03-10 was undetectable in plasma even after 1 hour regardless of the administration route. However, CB-03-10 metabolized to CB-03-05 with a body exposure of 189 (SC) and 47 (PO) hour/ng/ml (FIG. 14).

Example 22—In Vivo Testing of CB-03-10 in a Mouse Xenograft Model of Human Pancreatic Cancer (MiaPaca2 Cell Line)

Figure 15:
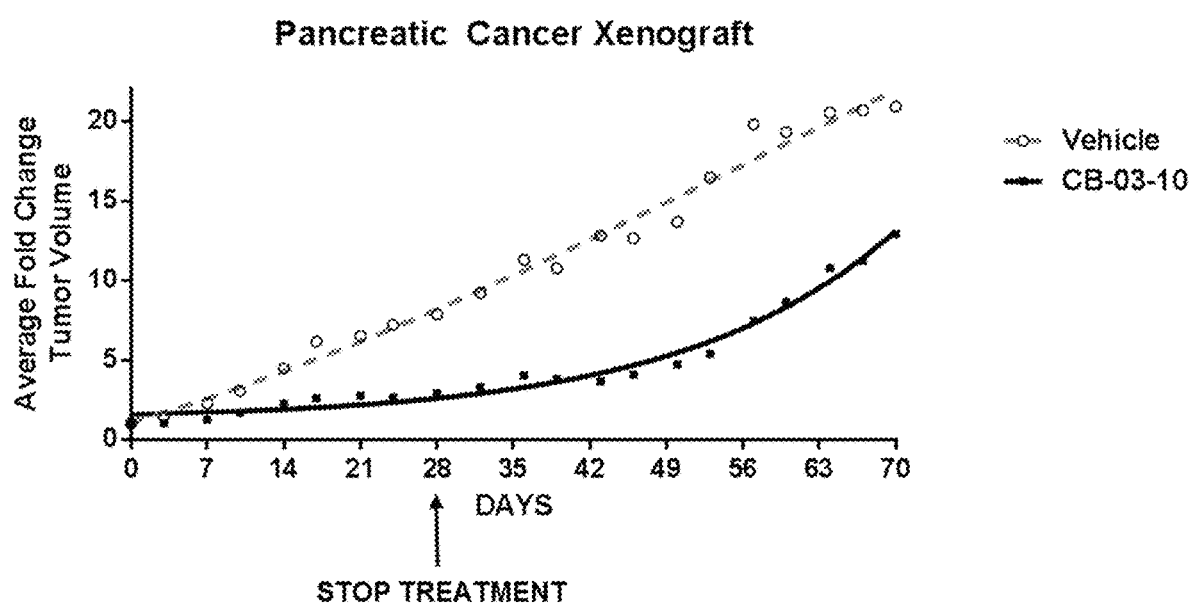
FIG. 15: CB-03-10 in vivo anti-tumor activity on mouse xenograft model of pancreatic cancer when administered subcutaneosly.

From previous studies CB-03-10 was observed to strongly inhibit the in vitro growth of MiaPaca2 pancreatic cells lines (AR$^{+/-}$). An investigation to whether this result could be translated into an in vivo xenograft pancreatic cancer model was performed. CPA a well-known antiandrogen was used as control. Briefly 1×10$^6$ MiaPaca2 cells suspended in matrigel were subcutaneously (SC) injected into 6 week old male athymic nude mice. Tumors were measured every 4 days with a digital caliper. Tumor volume was calculated according to the formula: 0.5236(r1) 2(r2) where r1<r2. Treatment with CB-03-10 and controls compounds was initiated after the tumor had reached 50 mm$^3$. Compounds diluted in DMSO/2-hydroxypropyl b-cyclodextrin (vehicle) were injected subcutaneously (SC) daily (100 μL/mouse) at the concentration of 40 mg/Kg daily for 28 consecutive days. FIG. 15 shows the average tumor increase in the in vivo xenograft model after SC injection of CB-03-10 when compared to the vehicle.

In FIG. 15, CB-03-10 shows a strong and significant in vivo anti-pancreatic tumor activity when compared to the controls. It also shows also a significant anti-tumor activity (p<0.5) when compared to vehicle only or CPA (not shown).

During the treatment period CB-03-10 maintained the pancreatic tumor size increase to less than 5-fold relative to the initial size. In contrast, the average tumor in the vehicle or CPA treatment groups increased in size to 12-fold. CB-03-10 besides inhibiting the tumor growth also showed a benefit in the mice survival. Importantly, 14 days after treatment was stopped, CB-03-10-treated mice still maintained significantly smaller tumors compared to the vehicle only group (6-fold vs 14-fold, respectively)

Median survival was 70 days for mice treated with CB-03-10 compared to 60 days for vehicle treated mice or 40 days with CPA. This difference is significant with a 2 to 4 time higher risk of death in the vehicle treated group.

Example 23—In Vivo Testing of CB-03-10 Administered Orally in a Mouse Xenograft Human Prostate Cancer Model (LNCaP Cells)

Figure 16:
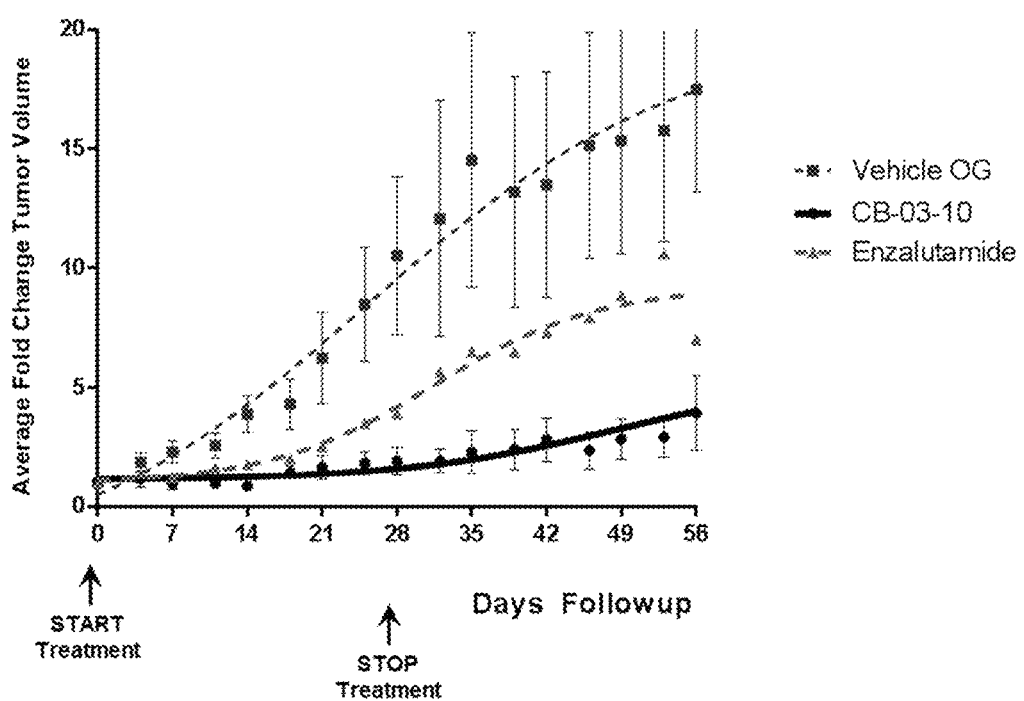
FIG. 16: CB-03-10 in vivo anti-tumor activity in a mouse xenograft model of prostate cancer when administered by oral gavage. Enzalutamide (Enza) a potent anti prostate cytotoxic drug is used as positive control. Our results show that the CB-03-10 Vs. vehicle is statistically significantly different from day 7 up to day 60. In contrast, Enzalutamide Vs. vehicle is statistically significant only on days 14 and 25. This comparison shows that CB-03-10 reaches a high statistical significance versus vehicle whereas Enzalutamide does not reach statistical significance versus vehicle.
Figure 17:
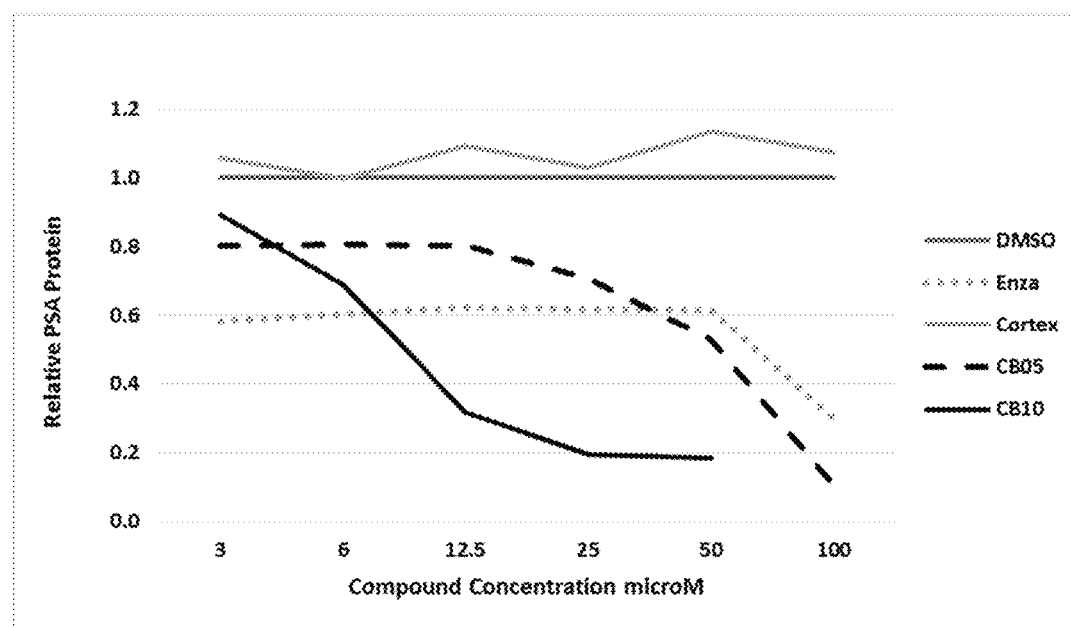
FIG. 17; CB-03-10 and CB-03-05 inhibition of in vitro baseline PSA secretion from LNCaP cancer cell lines.

From previous studies CB-03-10 was observed to be also effective in inhibiting in vitro the growth of LNCaP prostate cancer cells lines. An investigation to whether this result could be translated into an in vivo xenograft prostate cancer model was performed. 3×10$^6$ LNCaP cells suspended in matrigel were subcutaneously injected (on the right flank) into 6 week old male athymic nude mice. Tumors were measured as described above. Treatment with CB-03-10 and controls compounds was initiated after the tumor had reached 50 mm$^3$. Formulations for dosing were prepared in 15% Vitamin E-TPGS and 65% of a 0.5% w/v CMC solution in 20 mM citrate buffer (pH 4). Oral dosing was daily (100 mg/Kg in 200 μL/mouse) for 28 consecutive days. Results were plotted as average change in tumor volume relative to the start of treatment. FIG. 16 shows the results obtained from the in vivo xenograft prostate cancer model after oral administration of CB-03-10. Enzalutamide a novel and potent anti-androgen was used as positive control.

The oral administered CB-03-10 showed a better antitumor activity than Enzalutamide during the treatment period of 28 days. The tumor volume increased to only 2-fold with CB-03-10 and 3-fold with Enzalutamide compared to 10-fold in the negative control group.

CB-03-10 is also more effective than Enzalutamide in maintaining a small prostate tumor size increase after treatment was stopped (5 vs 8-fold change). Even 6 weeks after treatment was stopped, the average tumor volume in the CB-03-10 group was 3.6-times smaller than in the vehicle group.

Example 24—CB-03-10 Inhibition of In Vitro Prostate-Specific Antigen (PSA) Secretion from LNCaP Prostate Cancer Cells Prostate-specific antigen, or PSA, is a protein produced by cells of the prostate gland.

The PSA test measures the level of PSA in a man's blood. The blood level of PSA is often elevated in men with prostate cancer and it used as surrogate marker to test prostate cancer progression in human population. After the observation that CB-03-10 was able to inhibit in vivo the growth of prostate cancer, the capability of the compound to inhibit in vitro PSA secretion from cancer cells was determined. LNCaP cells were seeded in 96 well flat bottom culture plates in media containing charcoal stripped serum with or without 10 nM DHT. After 24 hours test compounds are added to cells, using DMSO as the vehicle negative control and Enzalutamide as the positive control. After 48 hours incubation with test compounds, supernatants were harvested and tested with an Elisa assay for PSA and same cells were lysed for cell viability assessment.

As expected the pure anti-androgen, Enzalutamide, is potent at inhibiting PSA secretion with an $IC_{50}$<3 μM; CB-03-10 is also potent PSA inhibitor ($IC_{50}$ 9 μM). However Enzalutamide activity did not titrate as well as CB-03-10. Of note, Cortexolone, the parent and final metabolite of all tested compounds, is essentially inactive on PSA secretion ($IC_{50}$ of 612 μM). When cell viability of these cells was tested, Enzalutamide showed an $IC_{50}$ of 61 μM and CB-03-10 showed an $IC_{50}$ of 11 μM. This confirms the strong growth inhibitory activity of both compounds. Importantly and interestingly, Cortexolone the parent and final metabolite of all tested compounds, inhibited LNCaP viability only at very high concentration ($IC_{50}$ of 153 μM) and it is essentially inactive as cytotoxic compound for cancer cell lines.

Example 25—Analysis of In Vitro Anti-Cancer Activity of CB-03-10 on Breast Cancer Cell Lines Triple Negative Breast Cancer (TNBC) accounts for around 20% of newly diagnosed invasive breast cancer. This subtype of cancer is not supported by hormones estrogen and progesterone, nor by the presence of too many HER2 receptors, for this reason patients do not respond to conventional therapy (eg tamoxifen or Herceptin). Consequently, this cancer is characterized by resistance to chemotherapy and low survival in patients.

There is a correlation between this cancer resistance and high GR expression (Cancer therapy 2013). There are clinical trials testing a GR antagonist (Mifepristone/RU486) in combination with chemotherapy for the treatment of TNBC. However mifepristone clinical use is compromised due to poly pharmacology tied to progesterone receptor (PR) antagonism. To evaluate if CB-03-10 can be used as potential treatment for breast cancer, and in particular TNBC, a cytotoxic assays was performed using breast cancer cell lines characterized by various hormone receptor expression The breast cancer cell lines selected for this assay were:
MCF7 breast cancer cells ($ER^+PR^+Her2^+$, $GR^{+/-}$)
MDA-MB-231 TBNC cells ($ER^-PR^-Her2^-$, $GR^{++}$)

Figure 18:
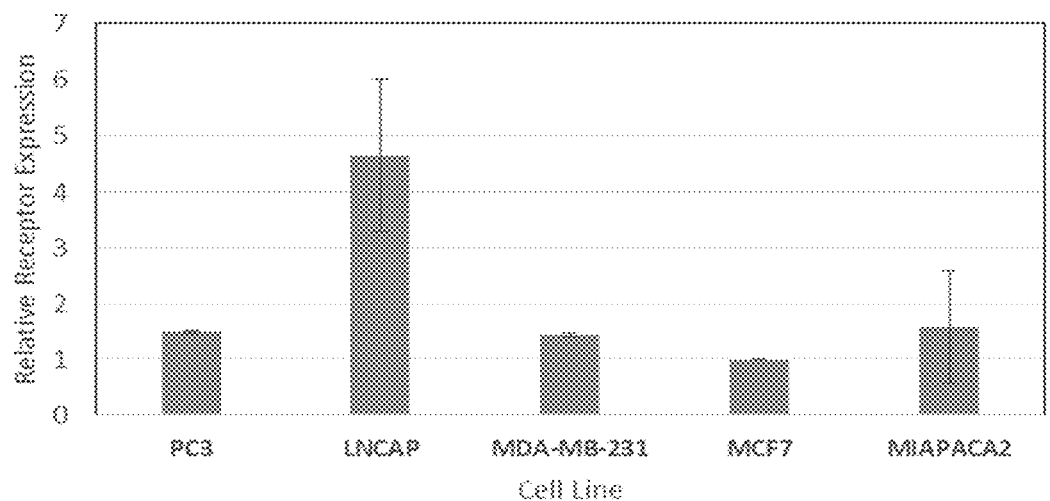
FIG. 18: Androgen and Glucorticoid receptor expression in different cancer cell lines.
Figure 18:
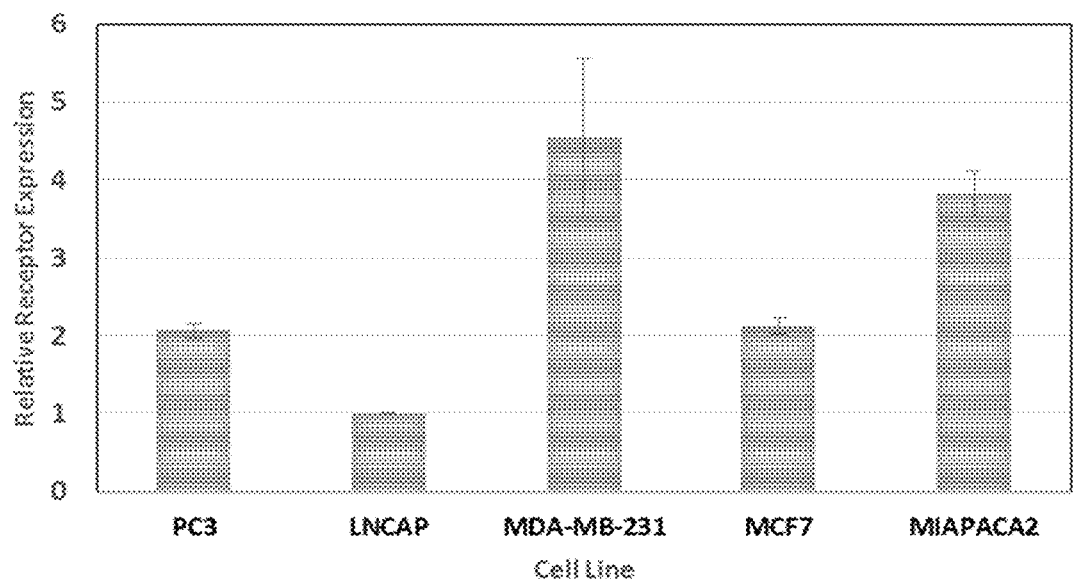

Before testing cell growth inhibition breast cancer cells were characterized for AR and GR receptor expression by FACS as previously described. The data shown in FIG. 18 confirms the receptor expression as indicated in the literature.

For the cytotoxic assay: cells seeded in 96 well flat bottom culture plates in media containing charcoal stripped serum. After 24 hours test compounds were added to the cells. DMSO was used as the vehicle negative control and RU486 as the positive control. After 72 hours incubation cell were harvested, lysed and viability determined using the cell titer glow assay for viability.

Table VI shows the $IC_{50}$ of CB-03-10 on the above mentioned breast cancer cells lines

|  | MCF7 ($ER^+PR^+GR^{+/-}$) | MDA-MB-231 ($ER^-PR^-GR^{++}$) |
|---|---|---|
| RU486 | Not active | 435 |
| CB-03-10 | 28 | 106 |
| CB-03-05 | 50 | Not active |

CB-03-10 is active on both breast cancer cell lines, but it seems more active in MCF7 cells than MDA-MB-231, perhaps hinting that GR is not the only target of this compound. RU486, mifepristone, (GR/PR antagonist) does not affect, as expected, viability of $GR^{+/-}$MCF7 cells, while inhibits, at a very low extent, the viability of TNBC $GR^+$MDA-MB-231 cells to a maximum of 25% at 100 μM. Interestingly, CB-03-05 is only active in MCF7, not in MDA-MB-231. It is not clear which receptor is responsible for this differential effect because these cells are different for at least 4 receptors. If not GR, then could be ER (Estrogen Receptor) (ER), PR (Progesterone Receptor) or Her2 which are expressed in MCF7 but not MDA MDA-MB-231.

GENERAL CONCLUSION

These examples demonstrate that Cortexolone 17α-valerate-21-propionate (CB-03-10), in particular, has a superior activity beyond other known cortexolone derived compounds. We have observed increased results both in-vitro and in-vivo in terms of, for example:

I) general in-vitro anti-tumoral activity;

II) in-vitro anti-tumoral activity not directly correlated to AR expression;

III) in-vitro anti-tumoral activity directly correlated to GR expression;

IV) therapeutic index (TI); and

V) In vivo anti-tumoral activity against pancreatic and prostate tumors;

VI) It is clear from the data shown in Table I reproduced below that cortexolone derived compounds kill cancer cells at various concentration and $IC_{50}$. However, CB-03-06 and CB-03-10 show the best $IC_{50}$ when compared to the other compounds in the cortexolone derived series across cancer cell lines of different origin. Even the metabolite CB-03-05 of CB-03-10, show good IC50 value in LNCaP prostate cancer cells ($IC_{50}$ 32 microM). The lower $IC_{50}$ depose for a stronger in vitro anti-tumoral activity.

TABLE I $IC_{50}$ of Cortexolone-derived Compounds tested in Prostate & Pancreatic Cancer Cell Lines

| Cell Line Name | CB-03-01 C17 prop | CB-03-03 C17, 21 but | CB-03-04 9dehy 17 but | CB-03-05 C17 val | CB-03-06 C17 ben | CB-03-10 C17, 21 val | Enza lutamide | CPA |
|---|---|---|---|---|---|---|---|---|
| LNCaP | 33 | 16 | 46 | 32 | 12 | 10 | 38 | 22 |
| PC3 | 190 | 53 | 140 | 170 | 28 | 53 | 180 | 90 |
| Panc1 | 490 | 70 | 340 | 74 | 28 | 60 | 110 | 46 |
| MiaPaca2 | 110 | 30 | 160 | 59 | 20 | 37 | 65 | 39 |

II) AR expression was tested on the cancer cell lines, see Table II reproduced below.

In prostate cancer cell lines, as expected, the growth inhibition shown by potent anti-androgens like CPA and Enzalutamide correlates with the AR expression in prostate cancer cells (higher is the AR expression better is the cytotoxic activity, expressed as lower $IC_{50}$). Also CB-03-04 shows an $IC_{50}$ of 46 when tested on LNCaP (prostate cancer cell line that express high level of Androgen Receptor) but an $IC_{50}$ much higher (135) when tested on PC3 that express low or null AR. Notably the cytotoxic activity of CB-03-06 and CB-03-10 is not evidently influenced by the Androgen Receptor expression on prostate cancer cells. CB-03-06 and CB-03-10 are characterized by a very good $IC_{50}$ almost irrespective of the AR expression.

In pancreatic cancer cell lines, where the AR expression was low or almost null CB-03-06 and CB-03-10 show a potent cytotoxic activity, higher then CPA and enzalutamide. The higher activity could be due to an additional mechanism of action related to the binding to additional receptors.

IV) Triple negative breast cancer (TNBC) as shown in example 25. The cytotoxic activity shown by CB-03-10 is particularly impressive because usually conventional therapeutic agents do not work on triple negative breast cancer (TNBC) cell lines. TNBC is defined as the absence of estrogen and progesterone receptor expression as well as ERBB2 amplification. It has no response to endocrine or anti-ERBB2 therapies. Recent studies have found some potential therapeutic targets for TNBC. However, it still has a poor outcome. Taking into consideration the cytotoxic activity and the excellent safety profile of CB-03-10; CB-03-10 is a new and improved candidate for the clinical treatment of this cancer.

The invention will now be described by the following numbered embodiments.

1. In one embodiment the invention is a compound of formula (I)

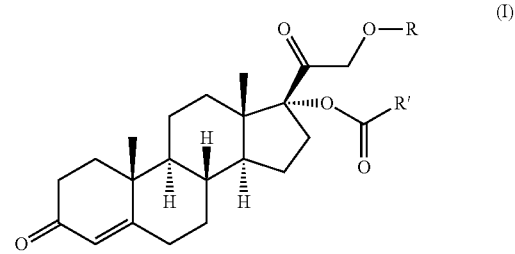

TABLE II

AR expression of Prostate & Pancreatic Cancer Cell Lines and $IC_{50}$ of Cortexolone-derived Compounds

| Cell Line Name | CB-03-01 C17 prop | CB-03-03 C17, 21 but | CB-03-04 9dehy 17 but | CB-03-05 C17 val | CB-03-06 C17 ben | CB-03-10 C17, 21 val | Enza lutamide | CPA | AR Expression |
|---|---|---|---|---|---|---|---|---|---|
| LNCaP | 33 | 16 | 46 | 32 | 12 | 10 | 38 | 22 | 9 |
| PC3 | 190 | 53 | 140 | 170 | 28 | 53 | 180 | 90 | 1 |
| Panc1 | 490 | 70 | 340 | 74 | 28 | 60 | 110 | 46 | 4 |
| MiaPaca2 | 110 | 30 | 160 | 59 | 20 | 37 | 65 | 39 | 1 |

III) The therapeutic index (TI) (also referred to as therapeutic window, safety window, or therapeutic ratio) is a comparison of the amount of a therapeutic agent that causes the therapeutic effect to the amount that causes toxicity. $IC_{50}$ of the compounds was determined on fresh cells isolated from human blood (PBMC). The compound toxicity was determined as follow:

Therapeutic Index=Safety/Potency=$IC_{50}$ stimulated PBMC/ $IC_{50}$ cancer cell The results are shown in Table VII. All cortexolone derived compounds show a robust safe toxicity profile. However CB-03-06 and CB-03-10 showed the highest therapeutic index when tested across all 7 cancer cell lines tested in vitro.

TABLE VII

Therapeutic index of cortexolone derived compounds on a panel of cancer cell lines
Therapeutic Index = IC50 stimulated PBMC/IC50 cancer cell

| Tissue Type | Cell Line Name | CB-03-01 C17 prop | CB-03-03 C17, 21 but | CB-03-04 9dehy 17 but | CB-03-05 C17 val | CB-03-06 C17 ben | CB-03-10 C17, 21 val | Enza lutamide | CPA |
|---|---|---|---|---|---|---|---|---|---|
| Prostate Cancer | LNCaP | 0 | 9 | 8 | 4 | 8 | 9 | 2 | 3 |
| | PC3 | 0 | 3 | 3 | 1 | 3 | 2 | 1 | 1 |
| Pancreatic Cancer | Panc1 | 0 | 2 | 1 | 2 | 3 | 2 | 1 | 1 |
| | MiaPaca2 | 0 | 5 | 2 | 2 | 5 | 3 | 1 | 2 |
| | BxPC3 | | | | | 3 | 3 | 1 | |
| Breast Cancer | MCF7 | 0 | 4 | 4 | 3 | 4 | 3 | 1 | 1 |
| Colon Cancer | HT29 | | | 7 | 4 | 6 | 3 | | |
| AVERAGE | | 0 | 4 | 4 | 3 | 5 | 4 | 1 | 1 | wherein R is hydrogen or C(O)—R₁, wherein R₁ is a linear alkyl chain containing 2 to 5 carbon atoms, and wherein R' is a linear alkyl chain containing 3 to 6 carbon atoms or an optionally substituted aryl group or an optionally substituted heteroaryl group.

2. In another embodiment the invention is a compound of formula (I) according to statement 1 wherein the optionally substituted aryl group is phenyl.
3. In another embodiment the invention is a compound of formula (I) according to statement 1 wherein R₁ is hydrogen or CH₂CH₃, and R' is —(CH₂)₃—CH₃ or phenyl.
4. In another embodiment the invention is a compound according to statement 1 having formula:

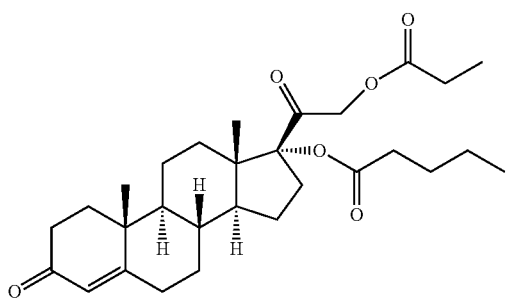

5. In another embodiment the invention is a compound according to statement 1 having formula:

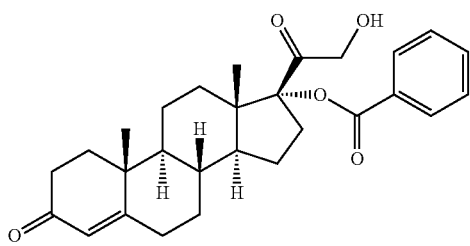

6. In another embodiment the invention is a compound according to any of statements 1 to 5 for use as a medicament.
7. In another embodiment the invention is a compound according to any of statements 1 to 5 for use in the treatment of precancerous lesions, dysplasias, metaplasias and tumor diseases.
8. In another embodiment the invention is a compound for use according to statement 7, characterized in that said tumor disease includes malignant neoplasias and metastasis.
9. In another embodiment the invention is a compound for use according to statement 8, characterized in that said tumor diseases are solid tumors, preferably epithelial tumors, such as prostate carcinoma; mammary carcinoma; pancreatic carcinoma; lung carcinoma; gastrointestinal tract carcinoma, such as colon carcinoma; kidney cancer; thyroid carcinoma; uterine carcinoma; adrenal carcinoma.
10. In another embodiment the invention is a compound for use according to statement 9, characterized in that said epithelial tumors are prostate carcinoma or pancreatic carcinoma, preferably exocrine pancreatic carcinoma.

11. In another embodiment the invention is a pharmaceutical composition comprising at least one compound of formula (I) according to any of statements 1 to 5, in association with at least one physiologically acceptable excipient.
12. In another embodiment the invention is pharmaceutical compositions according to statement 11, characterized in that they are in solid or in liquid form.
13. In another embodiment the invention is pharmaceutical compositions in solid form according to statement 12, characterized by being powders, freeze-dried powders, granules, pellets, tablets or capsules.
14. In another embodiment the invention is pharmaceutical compositions in liquid form according to statement 12, characterized by being solutions, emulsions, suspensions or syrups.
15. In another embodiment the invention is a pharmaceutical composition according to any of statements 11 to 14, characterized by containing at least another active ingredient, preferably a chemotherapeutic active ingredient, as a combination for simultaneous, separate or sequential administration.
16. In another embodiment the invention is a pharmaceutical composition according to statements 11 to 15 for use in the treatment of precancerous lesions, dysplasias, metaplasias and tumor diseases.
17. In another embodiment the invention is a pharmaceutical composition for use according to statement 16, characterized in that said tumor diseases include malignant neoplasias and metastasis.
18. In another embodiment the invention is a pharmaceutical composition for use according to statement 17, characterized in that said tumor diseases are solid tumors, preferably epithelial tumors, such as prostate carcinoma; mammary carcinoma; pancreatic carcinoma; lung carcinoma; gastrointestinal tract carcinoma, such as colon carcinoma; kidney cancer; thyroid carcinoma; uterine carcinoma; adrenal carcinoma.
19. In another embodiment the invention is a pharmaceutical composition for use according to statement 18, characterized in that said epithelial tumors are prostate carcinoma or pancreatic carcinoma, preferably exocrine pancreatic carcinoma.

What is claimed is:
1. A method of treating pancreatic carcinoma in a subject in need thereof, comprising treating said subject with a therapeutically effective amount of a compound of formula:

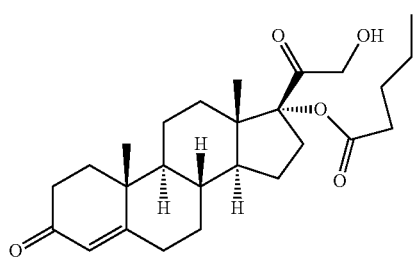

cortexolone 17α-valerate

2. The method of claim 1, wherein the pancreatic carcinoma is exocrine pancreatic carcinoma.

* * * * *